United States Patent
Lund et al.

(10) Patent No.: US 7,989,172 B2
(45) Date of Patent: Aug. 2, 2011

(54) METHOD OF IDENTIFYING A COMPOUND CAPABLE OF MODULATING THE TH2 POLARIZATION OF CD4+ LYMPHOCYTES

(75) Inventors: Riikka Lund, Raisio (FI); Riitta Lahesmaa, Turku (FI)

(73) Assignee: Turun Yliopisto, Turun Yliopisto (FI)

( * ) Notice: Subject to any disclaimer, the term of this patent is extended or adjusted under 35 U.S.C. 154(b) by 593 days.

(21) Appl. No.: 11/662,878

(22) PCT Filed: Sep. 16, 2005

(86) PCT No.: PCT/FI2005/050320
§ 371 (c)(1),
(2), (4) Date: Oct. 15, 2007

(87) PCT Pub. No.: WO2006/030071
PCT Pub. Date: Mar. 23, 2006

(65) Prior Publication Data
US 2008/0168570 A1    Jul. 10, 2008

(30) Foreign Application Priority Data

Sep. 16, 2004  (FI) ..................... 20041204

(51) Int. Cl.
*G01N 33/53*  (2006.01)
*G01N 33/567*  (2006.01)

(52) U.S. Cl. ......... 435/7.1; 435/7.2; 435/7.21; 435/7.24
(58) Field of Classification Search .................. None
See application file for complete search history.

(56) References Cited

U.S. PATENT DOCUMENTS

| | | |
|---|---|---|
| 6,414,117 B1 | 7/2002 | Levinson |
| 6,562,343 B1 | 5/2003 | Levinson |
| 2002/0039734 A1 | 4/2002 | Hanrahan et al. |
| 2003/0099963 A1 | 5/2003 | Morris et al. |
| 2003/0186377 A1 | 10/2003 | Glimcher et al. |
| 2007/0020618 A1 | 1/2007 | Prashar et al. |
| 2007/0020637 A1 | 1/2007 | Isogai et al. |

FOREIGN PATENT DOCUMENTS

| | | |
|---|---|---|
| EP | 1 440 981 A2 | 7/2004 |
| WO | WO-99/57130 A1 | 11/1999 |
| WO | WO-01/79555 A2 | 10/2001 |
| WO | WO-01/88199 A2 | 11/2001 |
| WO | WO-02/28999 A2 | 4/2002 |
| WO | WO-2004/083366 A2 | 9/2004 |

OTHER PUBLICATIONS

Anderson et al., Ann Hematol., 2000, vol. 79, No. 9, pp. 507-513.
Szabo et al., Cell, Mar. 17, 2000, vol. 100, pp. 655-669.
Lund et al., The Journal of Immunology, 2003, vol. 171, pp. 5328-5336.
Kato et al., Cellular Immunology, 2003, vol. 224, pp. 29-37.
Hamalainen et al., Genome Biology, 2001, vol. 2, No. 7, pp. 1-11.
Database Geneseq., accession No. ADY17747, May 5, 2005, retrieved from EBI, 100% Identity to NM_013351.

*Primary Examiner* — Prema Mertz
(74) *Attorney, Agent, or Firm* — Birch, Stewart, Kolasch & Birch, LLP

(57) ABSTRACT

The present invention provides methods utilizing novel target genes related to immune-mediated diseases, such as asthma, allergy and autoimmune diseases. The invention is based on a molecular level description of the polarization of CD4+ precursor cells (Thp) from which T helper cells are known to originate. Particularly, the present invention provides a method of identifying a compound capable of modulating the polarization of CD4+ lymphocytes. The invention is also related to a method for assessing the presence of, or disposition to, an immune-related disorder in a subject.

5 Claims, 2 Drawing Sheets

US 7,989,172 B2

Figure 1:
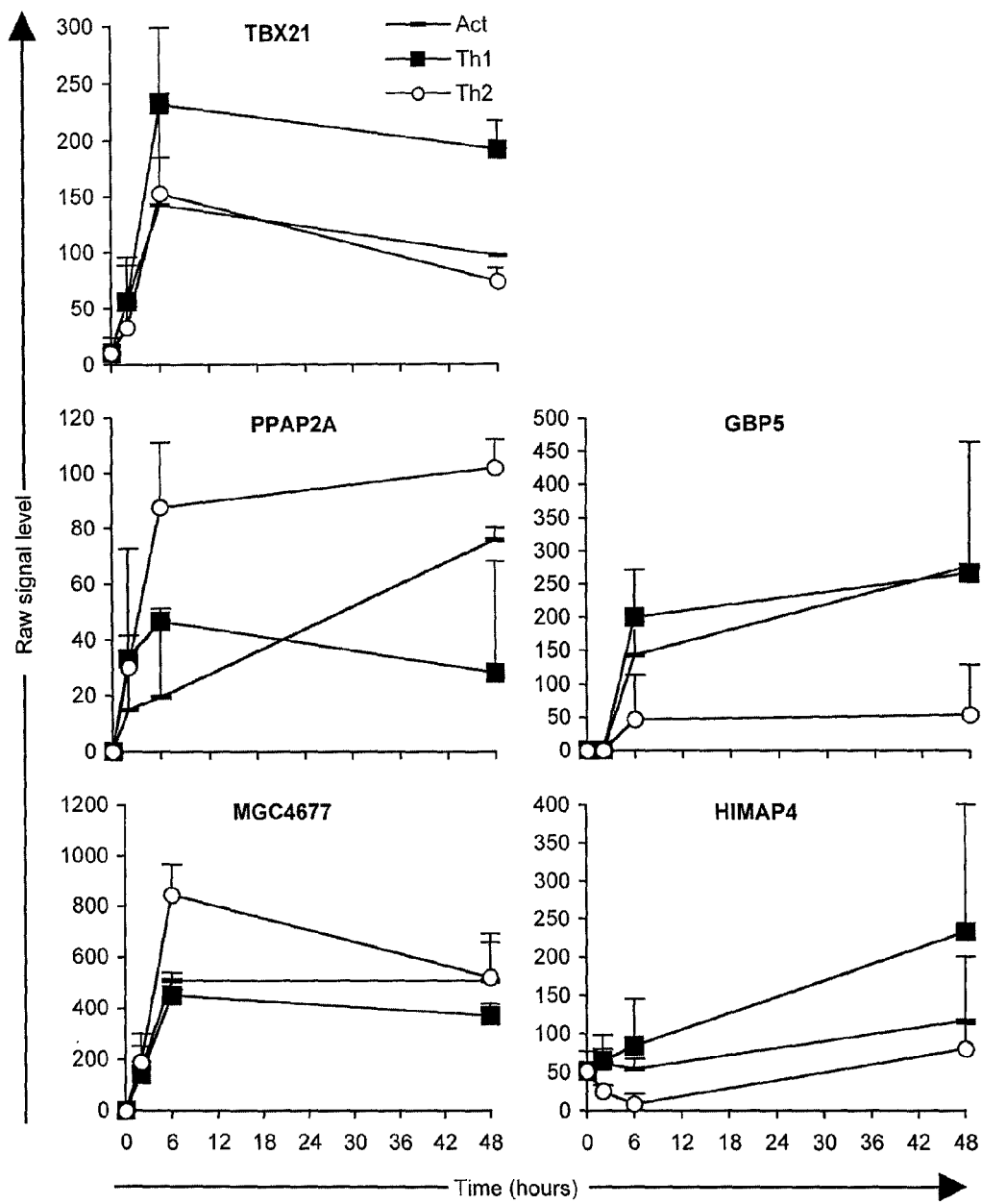

METHOD OF IDENTIFYING A COMPOUND CAPABLE OF MODULATING THE TH2 POLARIZATION OF CD4+ LYMPHOCYTES

This Application is the National Phase application under 35 U.S.C. § 371 of PCT International Application No. PCT/FI2005/050320 which has an International filing date of Sep. 16, 2005, which claims priority to Finnish Application No. 20041204 filed on Sep. 16, 2004.

FIELD OF THE INVENTION

The present invention provides methods utilizing novel target genes related to immune-mediated diseases, such as asthma, allergy and autoimmune diseases. The invention is based on a molecular level description of the polarization of CD4+ precursor cells (Thp) from which T helper cells are known to originate. T helper cell subtypes (Th1 and Th2) have an important role in the immune system. However, many pathological processes, such as allergies, are associated with the presence of T helper cells at the site of inflammation.

BACKGROUND

T helper cell subtypes Th1 and Th2 originate from common naïve precursor cells (Thp) in response to antigen and cytokine stimulation. Although, Th cells have a crucial role in host defence against intracellular and extracellular pathogens, disturbances in the balance between Th1 and Th2 responses can promote or lead to pathogenesis of immune-mediated diseases. Enhanced Th2 responses are involved in atopic diseases, such as asthma, whereas dominating Th1 responses are implicated in certain autoimmune diseases, such as type 1 diabetes or rheumatoid arthritis (1). For understanding the molecular mechanisms driving the pathogenesis of these diseases, it is essential to elucidate the early differentiation process of Th1 and Th2 cells in detail.

Some of the central factors involved in directing the differentiation process have been identified. IL12/STAT4 and IFNγ/STAT1 signaling are important in driving Th1 polarization, whereas IL4/STAT6 signaling directs Th2 polarization (2). Transcription factors TBX21 and GATA3 are also among the key factors required for the Th1 and Th2 differentiation, respectively (3-6). Although many players implicated in the regulation of differentiation have been recognized, the current model as such is still too simple to explain the process in detail and also other factors must be involved.

Recently, increasing number of studies has utilized DNA microarrays to identify new factors involved in the Th1 and Th2 polarization in human and mouse (7-14). However, all of these studies have focused on studying limited number of primarily known genes. In our recent studies we have elucidated regulation of approximately 9300 genes with primarily known function during the early differentiation of human Th1 and Th2 cells (10), (unpublished data). In this study we have extended the previous work by exploring the regulation of the rest of genes in the human genome. Based on current and our previous studies altogether 297 genes, representing approximately 1% of the human genome, are involved in the early Th1 and Th2 cell polarization during the first two days.

SUMMARY

Certain methods of the invention are related to a method of identifying a compound capable of modulating the polarization of CD4+ lymphocytes. The method includes the steps of contacting the compound with naïve CD4+ lymphocytes, and then inducing the polarization of the cells. Further, a gene expression profile from the lymphocytes is prepared during the polarization, and the profile is compared to a baseline gene expression profile of CD4+ lymphocyte polarization as established in Table 2, 3, 5, 6, and/or 7. A difference in the expression profiles of the target genes identifies a potential drug compound for the treatment of asthma or other immune-mediated diseases.

The invention is also related to a methods of identifying a compound that modulates the expression or activity of at least one target gene listed in Table 2, 3, 5, 6, and/or 7. The methods include the steps of (a) incubating a cell that can express a protein from said gene or a cell that has said activity with a compound under conditions and for a time sufficient for the cell to express the protein or activity of said gene, when the compound is not present, (b) incubating a control cell under the same conditions and for the same time without the compound, (c) measuring expression or activity of said gene in the cell in the presence of the compound; (d) measuring expression or activity of said gene in the control cell; and (e) comparing the amount of expression or activity of said gene in the presence and absence of the compound, wherein a difference in the level of expression or activity indicates that the compound modulates the expression of said gene.

Other methods that are provided are to identify a compound that modulates differentiation of a lymphocyte. These methods generally involve contacting a test cell capable of expressing one or more gene markers listed in Table 2, 3, 5, 6, and/or 7 with a test compound. The expression level of the one or more gene markers in the test cell is determined. The expression level of these gene markers are than compared with the expression levels for these same markers in a control cell. In these methods, the test cell and the control cell are lymphocytes and the cellular state of the control cell is known. A difference in the expression level between the test and control cell is an indicator that the test compound is a modulator of lymphocyte differentiation.

Another embodiment of the invention relates to a method of treating a patient with asthma or other immune-mediated disease. The method of treatment comprises administering to the patient a pharmaceutical composition that alters the expression or activity of at least one gene listed in Table 2, 3, 5, 6, and/or 7. In a preferred embodiment of the invention, the active compound of said pharmaceutical composition is identified by a method of the invention.

Methods for classifying a lymphocyte or assessing the cellular state of a lymphocytic cell are also provided. Certain of these methods involve providing a test sample derived from the lymphocyte, wherein the lymphocyte is capable of expressing one or more nucleic acid markers from the group consisting of those listed in one or more of the tables (e.g. Table 2, 3, 5, 6, and/or 7). The expression level of the one or more markers in the test sample are determined and compared with the expression level of the same markers in a control sample. The control sample is derived from a lymphocytic cell whose cellular status is known. The lymphocyte is then classified on the basis of this comparison. In some instances, the methods involve classifying the lymphocyte as being a Th1 or Th2 type cell.

A variety of methods for diagnosing the presence of, or a predisposition to, an immune-related disease are provided as well. These methods generally involve determining the expression level of one or more nucleic acid markers in a test sample obtained from a subject. These markers are selected from the group consisting of those listed in one or more of the tables (e.g. Table 2, 3, 5, 6, and/or 7). The expression level of the one or more nucleic acid markers in the test sample is compared with the expression level of the same markers in a control sample whose immune status is known. The presence or absence of the immune disorder in the subject, or a predisposition to the immune disorder, is then diagnosed on the basis of this comparison.

A BRIEF DESCRIPTION OF THE DRAWING

FIG. 1. Genes regulated in an opposite manner by IL12 and IL4. Expression profiles of the cells activated with anti-CD3+ anti-CD28 alone (Act) or in combination with IL12 (Th1) or IL4 (Th2) were studied with oligonucleotide arrays after 0, 2, 6, 24 and 48 h of polarization. In the figure the raw signals indicating the expression level of the genes are represented for those genes that were observed to be regulated by both IL12 and IL4 in an opposite manner.

Figure 2:
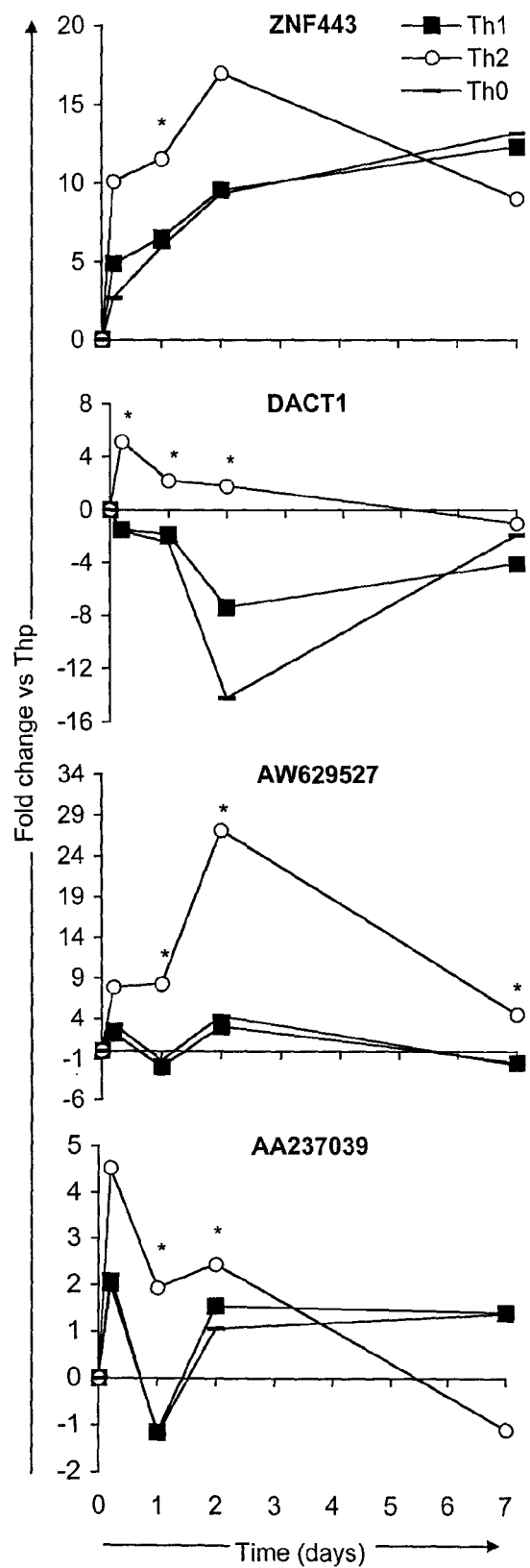

FIG. 2. Validation of the oligonucleotide array results with Real-Time RT-PCR. CD4+ T cells were isolated form human cord blood. The cell were activated with PHA and CD32-B7 transfected feeder cells and were cultured at "neutral conditions" (Th0) or were polarized to Th1 or Th2 for 7 days. During the polarization process expression of ZNF443, DACT1, AW629527 and AA237039 was studied at the indicated time points with Real-Time RT-PCR.

DETAILED DESCRIPTION

I. Definitions

The terms "nucleic acid," "polynucleotide" and "oligonucleotide" are used interchangeably and refer to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

The term "target nucleic acid" refers to a nucleic acid (often derived from a biological sample), to which a polynucleotide probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid can refer to the specific subsequence of a larger nucleic acid to which the probe is directed or to the overall sequence (e.g., gene or mRNA) whose expression level it is desired to detect.

A "probe" or "polynucleotide probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." A probe can include natural (i.e., A, G, C, or T) or modified bases (7-deazaguanosine, inosine, etc.). A probe can be an oligonucleotide which is a single-stranded DNA. Polynucleotide probes can be synthesized or produced from naturally occurring polynucleotides. In addition, the bases in a probe can be joined by a linkage other than a phosphodiester bond, so long as it does not interfere with hybridization. Thus, probes can include, for example, peptide nucleic acids in which the constituent bases are joined by peptide bonds rather than phosphodiester linkages (see, e.g., Nielsen et al., *Science* 254, 1497-1500 (1991)). Some probes can have leading and/ or trailing sequences of noncomplementarity flanking a region of complementarity.

A "perfectly matched probe" has a sequence perfectly complementary to a particular target sequence. The probe is typically perfectly complementary to a portion (subsequence) of a target sequence. The term "mismatch probe" refer to probes whose sequence is deliberately selected not to be perfectly complementary to a particular target sequence.

A "primer" is a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides, although shorter or longer primers can be used as well. Short primer molecules generally require cooler temperatures to form sufficiently stable hybrid complexes with the template. A primer need not reflect the exact sequence of the template but must be sufficiently complementary to hybridize with a template. The term "primer site" refers to the area of the target DNA to which a primer hybridizes. The term "primer pair" means a set of primers including a 5' "upstream primer" that hybridizes with the 5' end of the DNA sequence to be amplified and a 3'"downstream primer" that hybridizes with the complement of the 3' end of the sequence to be amplified.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The terms "polypeptide," "peptide" and "protein" are used interchangeably to refer to a polymer of amino acid residues. The term also applies to amino acid polymers in which one or more amino acids are chemical analogues of a corresponding naturally occurring amino acids.

A "subsequence" or "segment" refers to a sequence of nucleotides or amino acids that comprise a part of a longer sequence of nucleotides or amino acids (e.g., a polypeptide), respectively.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

The terms "identical" or percent "identity," in the context of two or more nucleic acids or polypeptides, refer to two or more sequences or subsequences that are the same or have a specified percentage of nucleotides or amino acid residues that are the same, when compared and aligned for maximum correspondence, as measured using a sequence comparison algorithm such as those described below for example, or by visual inspection.

The phrase "substantially identical," in the context of two nucleic acids or polypeptides, refers to two or more sequences or subsequences that have at least 75%, preferably at least 85%, more preferably at least 90%, 95% or higher nucleotide or amino acid residue identity, when compared and aligned for maximum correspondence, as measured using a sequence comparison algorithm such as those described below for example, or by visual inspection. Preferably, the substantial identity exists over a region of the sequences that is at least about 30 residues in length, preferably over a longer region than 50 residues, more preferably at least about 70 residues, and most preferably the sequences are substantially identical over the full length of the sequences being compared, such as the coding region of a nucleotide for example. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see, e.g., *Current Protocols in Molecular Biology* (Ausubel et al., 1995 supplement).

One useful algorithm for conducting sequence comparisons is PILEUP. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity is the BLAST and the BLAST 2.0 algorithms, which are described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM 62 scoring matrix. The TBLATN program (using protein sequence for nucleotide sequence) uses as defaults a word length (W) of 3, an expectation (E) of 10, and a BLOSUM 62 scoring matrix. (See, e.g., Henikoff & Henikoff, *Proc. Natl. Acad. Sci. USA* 89:10915 (1989)).

Another indication that two nucleic acid sequences are substantially identical is that the two molecules hybridize to each other under stringent conditions. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide.

A further indication that two nucleic acid sequences or polypeptides are substantially identical is that the polypeptide encoded by the first nucleic acid is immunologically cross reactive with the polypeptide encoded by the second nucleic acid, as described below. The phrases "specifically binds to a protein" or "specifically immunoreactive with," when referring to an antibody refers to a binding reaction which is determinative of the presence of the protein in the presence of a heterogeneous population of proteins and other biologics. Thus, under designated immunoassay conditions, a specified antibody binds preferentially to a particular protein and does not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

A polypeptide is typically substantially identical to a second polypeptide, for example, where the two peptides differ only by conservative substitutions. A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well-known in the art. See, e.g., Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

The term "naturally occurring" as applied to an object refers to the fact that an object can be found in nature. For example, a polypeptide or polynucleotide sequence that is present in an organism that can be isolated from a source in nature and which has not been intentionally modified by humans in the laboratory is naturally occurring.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to VH-CH1 by a disulfide bond. The $F(ab)'_2$ may be reduced under mild conditions to break the disulfide linkage in the hinge region thereby converting the $(Fab')_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH::VL heterodimer which may be expressed from a nucleic acid including VH- and VL-encoding sequences either joined directly or joined by a peptide-encoding linker. Huston, et al. *Proc. Nat. Acad. Sci. USA*, 85:5879-5883 (1988). A number of structures for converting the naturally aggregated—but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRS" and are characterized, for example by Kabat et al. *Sequences of proteins of immunological interest*, 4th ed. U.S. Dept. Health and Human Services, Public Health Services, Bethesda, Md. (1987).

The term "antigenic determinant" refers to the particular chemical group of a molecule that confers antigenic specificity.

The term "epitope" generally refers to that portion of an antigen that interacts with an antibody. More specifically, the term epitope includes any protein determinant capable of specific binding to an immunoglobulin or T-cell receptor. Specific binding exists when the dissociation constant for antibody binding to an antigen is $\leq 1$ μM, preferably $\leq 100$ nM and most preferably $\leq 1$ nM. Epitopic determinants usually consist of chemically active surface groupings of molecules such as amino acids and typically have specific three dimensional structural characteristics, as well as specific charge characteristics.

The term "specific binding" (and equivalent phrases) refers to the ability of a binding moiety (e.g., a receptor, antibody, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ $M^{-1}$, and preferably at least about $10^7$, $10^8$, $10^9$, or $10^{10}$ $M^{-1}$.

A "subject" generally refers to an organism from which lymphocytes can be obtained. Usually the subject is a mammal. The mammal can be a primate (e.g., a human, monkey, ape, or chimpanzee), or a non-primate (e.g., a mouse).

II. Overview

Many biological functions are controlled through changes in the expression of various genes by transcriptional (e.g., through control of initiation, RNA processing, etc.) and/or translational control. For example, fundamental biological processes such as cell cycle, cell differentiation and cell death, are often characterized by the variations in the expression levels of groups of genes (see e.g. WO02059271). The changes in gene expression also are associated with pathogenesis. Thus, changes in the expression levels of particular genes can indicate the presence and progression of various diseases.

According to the invention, genes that are differentially expressed during cytokine induced CD4+ lymphocyte polarization in both the presence and absence of TGFβ have been discovered. One or more of these target genes can be used as part of an "an expression profile" that is representative of a particular state of a lymphocyte. Identification of these new target genes enable immune-mediated diseases to be analyzed more reliably. These results also provide new insights into T cell differentiation and reveal new potential target genes for the therapy of diseases such as asthma. These differentially expressed genes and their corresponding proteins can also be utilized as "markers" that characterize particular cellular states for lymphocytes.

The differentially expressed genes that have been identified can be utilized in a variety of methods for classifying lymphocytes, as well as diagnosing and treating immune-mediated diseases (e.g., asthma, allergic responses and autoimmune diseases). Kits and devices including one or more of the differentially expressed genes, proteins encoded by these genes and/or antibodies that bind the proteins are also provided.

For example, the differentially expressed genes can be used to in screening methods to identify compounds that modulate the expression or activity of the differentially expressed genes. Such methods can be utilized, for example, for the identification of compounds that can treat symptoms of disorders related to expression of proteins encoded by the differentially expressed genes. In addition, the invention encompasses methods for treating immune-mediated diseases or disorders by administering compounds and/or other substances that modulate the activity of one or more of the target genes or target gene products. Such compounds and other substances can effect the modulation either on the level of target gene expression or target protein activity. Certain classification methods that are also provided involve determining the level of one or more of the differentially expressed genes to determine whether a lymphocyte has been polarized in the Th1 or Th2 direction.

III. Differentially Expressed Genes

As described more fully in the examples below, an initial set of experiments were conducted to identify the gene expression profiles of CD4+ cells induced in the Th1 and Th2 directions in the presence and absence of TGFβ. This allowed those genes involved in early polarization to be identified, as well providing insight regarding which genes are involved in the immunosuppressive effect of TGFβ. Another set of experiments was then conducted to identify those genes in lymphocytes that are regulated by the cytokines IL-12 and IL-4. Most of the differentially expressed genes were identified using oligonucleotide arrays; the differential expression of certain genes was confirmed using real-time PCR approaches.

The differentially expressed genes include, for instance, those identified under the following sets of conditions or states:

(a) CD4+ cells activated by contact with CD3/CD28 versus unactivated CD4+ cells; these genes correspond to target genes of activation;

(b) activated CD4+ cells further activated with IL-12 versus activated CD4+ cells; these genes are representative of Th1 cells and correspond to target genes of IL-12;

c) activated CD4+ cells further activated with IL-4 versus activated CD4+ cells; these genes are representative of Th2 cells and correspond to target genes of IL-4;

(d) activated cells polarized with IL-12 exposed to TGFβ versus similar cells not exposed to TGFβ; these correspond to genes in Th1 cells that are affected by TGFβ;

(e) activated cells polarized with IL-4 exposed to TGFβ versus similar cells not exposed to TGFβ; these correspond to genes in Th2 cells that are affected by TGFβ; and (f) genes differentially expressed in Th1 cells versus Th2 cells.

As discussed in greater detail below, knowledge of the nucleic acids that are up-regulated or down-regulated in the various types of lymphocytes and in different cellular states provides the basis for a number of different screening, treatment and diagnostic methods, in addition to devices to carry out these methods. The differentially expressed genes include both "fingerprint genes" and "control genes." "Fingerprint genes" are those nucleic acids that correlate with a particular type of lymphocyte (e.g., Th1 or Th2), or a particular cellular state (e.g., activated or non-activated). As described in greater detail below, fingerprint genes can be used in the development of a variety of different screening and diagnostic methods to classify types of lymphocytes and/or to aid in the diagnosis of particular disease conditions. A "control gene" is one that encodes a protein that is involved in a lymphocyte assuming a particular state or becoming a particular type of cell. Because of the role such genes play, control genes are useful targets for the development of compound discovery programs and pharmaceutical development such as described infra. In some instances, a fingerprint gene can be a control gene and vice versa.

Expression levels for combinations of differentially expressed genes, in particular fingerprint genes, can be used to develop "expression profiles" that are characteristic of a particular type of lymphocyte or cellular state. Expression profiles as used herein refers to the pattern of gene expression corresponding to at least one differentially expressed genes, but typically includes a plurality of genes. For instance, an expression profile can include at least 1, 2, 3, 4 or 5 differentially expressed genes, but in other instances can include at least 6, 7, 8, 9, 10, 12, 14, 16, 18, 20, 25, 30, 35, 40, 45 or 50 or more differentially expressed genes. In some instances, expression profiles include all of the differentially expressed genes known for a particular type of lymphocyte or cellular state. So, for example, certain expression profiles include a measure (quantitative or qualitative) of the expression level for each of the differentially expressed genes in one or more of the tables or figures.

The pattern of expression associated with gene expression profiles can be defined in several ways. For example, a gene expression profile can be the absolute (e.g., a measured value) or relative transcript level of any number of particular differentially expressed genes. In other instances, a gene expression profile can be defined by comparing the level of expression of a variety of genes in one state to the level of expression of the same genes in another state (e.g., activated versus unactivated), or between one cell type and another cell type (e.g., Th1 versus Th2).

As used herein, the term "differentially expressed gene" or "differentially expressed nucleic acid" refers to the specific sequence as set forth in the particular GenBank entry that is provided herein (see, e.g., the tables and figures). The term, however, is also intended to include more broadly naturally occurring sequences (including allelic variants of those listed for the GenBank entries), as well as synthetic and intentionally manipulated sequences (e.g., nucleic acids subjected to site-directed mutagenesis). It is noted that the sequences of the target genes listed in the tables and figures are available in the public databases. The tables provide the accession number and name for each of the sequences. The sequences of the genes in GenBank are herein expressly incorporated by reference in their entirety as of the filing date of this application (see www.ncbi.nim.nih.gov).

Differentially expressed nucleic acids also include sequences that are complementary to the listed sequences, as well as degenerate sequences resulting from the degeneracy of the genetic code. Thus, the differentially expressed nucleic acids include: (a) nucleic acids having sequences corresponding to the sequences as provided in the listed GenBank accession number; (b) nucleic acids that encode amino acids encoded by the nucleic acids of (a); (c) a nucleic acid that hybridizes under stringent conditions to a complement of the nucleic acid of (a); and (d) nucleic acids that hybridize under stringent conditions to, and therefore are complements of, the nucleic acids described in (a) through (c). The differentially expressed nucleic acids of the invention also include: (a) a deoxyribonucleotide sequence complementary to the full-length nucleotide sequences corresponding to the listed GenBank accession numbers; (b) a ribonucleotide sequence complementary to the full-length sequence corresponding to the listed GenBank accession numbers; and (c) a nucleotide sequence complementary to the deoxyribonucleotide sequence of (a) and the ribonucleotide sequence of (b). The differentially expressed nucleic acids further include fragments of the foregoing sequences. For example, nucleic acids including 10, 12, 14, 16, 18, 20, 22, 24, 26, 28, 30, 40, 50, 60, 70, 80, 90, 100, 125, 150, 175, 200, 225, 250, 275 or 300 contiguous nucleotides (or any number of nucleotides therebetween) from a differentially expressed nucleic acid are included. Such fragments are useful, for example, as primers and probes for hybridizing full-length differentially expressed nucleic acids (e.g., in detecting and amplifying such sequences).

In some instances, the differentially expressed nucleic acids include conservatively modified variations. Thus, for example, in some instances, the differentially expressed nucleic acids are modified. One of skill will recognize many ways of generating alterations in a given nucleic acid construct. Such well-known methods include site-directed mutagenesis, PCR amplification using degenerate polynucleotides, exposure of cells containing the nucleic acid to mutagenic agents or radiation and chemical synthesis of a desired polynucleotide (e.g., in conjunction with ligation and/or cloning to generate large nucleic acids). See, e.g., Giliman and Smith (1979) *Gene* 8:81-97, Roberts et al. (1987) *Nature* 328: 731-734). When the differentially expressed nucleic acids are incorporated into vectors, the nucleic acids can be combined with other sequences including, but not limited to, promoters, polyadenylation signals, restriction enzyme sites and multiple cloning sites. Thus, the overall length of the nucleic acid can vary considerably.

Certain differentially expressed nucleic acids of the invention include polynucleotides that are substantially identical to a polynucleotide sequence as set forth in SEQ ID NO:1. Such nucleic acids can function as new markers for certain types of lymphocytes and for different cellular states for lymphocytes. For example, the invention includes polynucleotide sequences that are at least 80%, 85%, 90%, 92%, 94%, 96%, 98% or 100% identical to the polynucleotide sequences provided in the GenBank entries listed in the tables. Identity is typically measured over at least 40, 50, 60, 70, 80, 90 or 100 contiguous nucleotides. In other instances, identity is measured over a region of at least 150, 200, or 250 nucleotides in length. In yet other instances, the region of similarity exceeds 250 nucleotides in length and extends for at least 300, 350, 400, 450 or 500 nucleotides in length, or over the entire length of the sequence.

As described above, sequence identity comparisons can be conducted using a nucleotide sequence comparison algorithm such as those know to those of skill in the art. For example, one can use the BLASTN algorithm. Suitable parameters for use in BLASTN are wordlength (W) of 11, M=5 and N=−4 and the identity values and region sizes just described.

B. Preparation of Differentially Expressed Genes

The differentially expressed nucleic acids can be obtained by any suitable method known in the art, including, for example: (1) hybridization of genomic or cDNA libraries with probes to detect homologous nucleotide sequences; (2) antibody screening of expression libraries to detect cloned DNA fragments with shared structural features; (3) various amplification procedures such as polymerase chain reaction (PCR) using primers capable of annealing to the nucleic acid of interest; and (4) direct chemical synthesis.

The desired nucleic acids can also be cloned using well-known amplification techniques. Examples of protocols sufficient to direct persons of skill through in vitro amplification methods, including the polymerase chain reaction (PCR) the ligase chain reaction (LCR), Qβ-replicase amplification and other RNA polymerase mediated techniques, are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Improved methods of cloning in vitro amplified nucleic acids are described in Wallace et al., U.S. Pat. No. 5,426,039.

As an alternative to cloning a nucleic acid, a suitable nucleic acid can be chemically synthesized. Direct chemical synthesis methods include, for example, the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method described in U.S. Pat. No. 4,458,066. Chemical synthesis produces a single stranded polynucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences can be cloned and the appropriate subsequences cleaved using appropriate restriction enzymes. The fragments can then be ligated to produce the desired DNA sequence.

C. Utility of Differentially Expressed Nucleic Acids and Expression Profiles

As alluded to above and described in greater detail below, the differentially expressed nucleic acids that are provided can be used as markers in a variety of screening and diagnostic methods. For example, the differentially expressed nucleic acids find utility as hybridization probes or amplification primers. In certain instances, these probes and primers are fragments of the differentially expressed nucleic acids of the lengths described earlier in this section. Such fragments are generally of sufficient length to specifically hybridize to an RNA or DNA in a sample obtained from a subject. The nucleic acids are typically 10-30 nucleotides in length, although they can be longer as described above. The probes can be used in a variety of different types of hybridization experiments, including, but not limited to, Northern blots and Southern blots and in the preparation of custom arrays (see infra). The differentially expressed nucleic acids can also be used in the design of primers for amplifying the differentially expressed nucleic acids and in the design of primers and probes for quantitative RT-PCR. The primers most frequently include about 20 to 30 contiguous nucleotides of the differentially expressed nucleic acids to obtain the desired level of stability and thus selectivity in amplification, although longer sequences as described above can also be utilized.

Hybridization conditions are varied according to the particular application. For applications requiring high selectivity (e.g., amplification of a particular sequence), relatively stringent conditions are utilized, such as 0.02 M to about 0.10 M NaCl at temperatures of about 50° C. to about 70° C. High stringency conditions such as these tolerate little, if any, mismatch between the probe and the template or target strand of the differentially expressed nucleic acid. Such conditions are useful for isolating specific genes or detecting particular mRNA transcripts, for example.

Other applications, such as substitution of amino acids by site-directed mutagenesis, require less stringency. Under these conditions, hybridization can occur even though the sequences of the probe and target nucleic acid are not perfectly complementary, but instead include one or more mismatches. Conditions can be rendered less stringent by increasing the salt concentration and decreasing temperature. For example, a medium stringency condition includes about 0.1 to 0.25 M NaCl at temperatures of about 37° C. to about 55° C. Low stringency conditions include about 0.15M to about 0.9 M salt, at temperatures ranging from about 20° C. to about 55° C.

V. Proteins

A. General

The differentially expressed nucleic acids that have been identified can be inserted into any of a number of known expression systems to generate large amounts of the protein encoded by the gene or gene fragment. Such proteins can then be utilized in the preparation of antibodies. Proteins encoded by target genes can be utilized in the compound development programs described below and in the preparation of various diagnostics (e.g., antibody arrays).

The polypeptides can be isolated from natural sources, and/or prepared according to recombinant methods, and/or prepared by chemical synthesis, and/or prepared using a combination of recombinant methods and chemical synthesis. Besides substantially full-length polypeptides, biologically active fragments of the polypeptides are also provided. Biological activity can include, for example, antibody binding (e.g., the fragment competes with a full-length polypeptide) and immunogenicity (i.e., possession of epitopes that stimulate B- or T-cell responses against the fragment). Such fragments generally comprise at least 5 contiguous amino acids, typically at least 6 or 7 contiguous amino acids, in other instances 8 or 9 contiguous amino acids, usually at least 10, 11 or 12 contiguous amino acids, in still other instances at least 13 or 14 contiguous amino acids, in yet other instances at least 16 contiguous amino acids, and in some cases at least 20, 40, 60 or 80 contiguous amino acids.

Often the polypeptides will share at least one antigenic determinant in common with the amino acid sequence of the full-length polypeptide. The existence of such a common determinant is evidenced by cross-reactivity of the variant protein with any antibody prepared against the full-length polypeptide. Cross-reactivity can be tested using polyclonal sera against the full-length polypeptide, but can also be tested using one or more monoclonal antibodies against the full-length polypeptide.

The polypeptides include conservative variations of the naturally occurring polypeptides. Such variations can be minor sequence variations of the polypeptide that arise due to natural variation within the population (e.g., single nucleotide polymorphisms) or they can be homologs found in other species. They also can be sequences that do not occur naturally but that are sufficiently similar so that they function similarly and/or elicit an immune response that cross-reacts with natural forms of the polypeptide. Sequence variants can be prepared by standard site-directed mutagenesis techniques. The polypeptide variants can be substitutional, insertional or deletion variants. Deletion variants lack one or more residues of the native protein that are not essential for function or immunogenic activity (e.g., polypeptides lacking transmembrane or secretory signal sequences). Substitutional variants involve conservative substitutions of one amino acid residue for another at one or more sites within the protein and can be designed to modulate one or more properties of the polypeptide such as stability against proteolytic cleavage. Insertional variants include, for example, fusion proteins such as those used to allow rapid purification of the polypeptide and also can include hybrid proteins containing sequences from other polypeptides, which are homologues of the polypeptide. The foregoing variations can be utilized to create equivalent, or even an improved, second-generation polypeptide. Preparation of variants is well known in the art (see, e.g., Creighton (1984) *Proteins*, W.H. Freeman and Company, which is incorporated herein by reference in its entirety for all purposes).

The polypeptides that are provided also include those in which the polypeptide has a modified polypeptide backbone. Examples of such modifications include chemical derivatizations of polypeptides, such as acetylations and carboxylations. Modifications also include glycosylation modifications and processing variants of a typical polypeptide. Such processing steps specifically include enzymatic modifications, such as ubiquitinization and phosphorylation. See, e.g., Hershko & Ciechanover, *Ann. Rev. Biochem.* 51:335-364 (1982). Also included are mimetics, which are peptide-containing molecules that mimic elements of protein secondary structure (see, e.g., Johnson, et al., "Peptide Turn Mimetics" in *Biotechnology and Pharmacy*, (Pezzuto et al., Eds.), Chapman and Hall, New York (1993)). Peptide mimetics are typically designed so that side chain groups extending from the backbone are oriented such that the side chains of the mimetic can be involved in molecular interactions similar to the interactions of the side chains in the native protein.

B. Production of Polypeptides

1. Recombinant Technologies

The polypeptides encoded by the differentially expressed nucleic acids can be expressed in hosts after the coding sequences have been operably linked to an expression control sequence in an expression vector. Expression vectors are typically replicable in the host organisms either as episomes or as an integral part of the host chromosomal DNA. Expression vectors commonly contain selection markers, e.g., tetracycline resistance or hygromycin resistance, to permit detection and/or selection of those cells transformed with the desired DNA sequences (see, e.g., U.S. Pat. No. 4,704,362).

A differentially expressed gene typically is placed under the control of a promoter that is functional in the desired host cell to produce relatively large quantities of a polypeptide of the invention. An extremely wide variety of promoters are well known to those of skill, and can be used in the expression vectors, depending on the particular application. Ordinarily, the promoter selected depends upon the cell in which the promoter is to be active. Other expression control sequences such as ribosome binding sites, transcription termination sites and the like are also optionally included. Constructs that include one or more of such control sequences are termed "expression cassettes." Accordingly, expression cassettes are provided into which the differentially expressed nucleic acids are incorporated for high level expression of the corresponding protein in a desired host cell.

A wide variety of cloning and in vitro amplification methods suitable for the construction of recombinant nucleic acids is described, for example, in Berger and Kimmel, *Guide to Molecular Cloning Techniques, Methods in Enzymology*, Volume 152, Academic Press, Inc., San Diego, Calif. (Berger); and "Current Protocols in Molecular Biology," F. M. Ausubel et al. eds., *Current Protocols*, a joint venture between Greene Publishing Associates, Inc. and John Wiley & Sons, Inc., (1998 Supplement) (Ausubel).

2. Naturally Occurring Polypeptides

Naturally occurring polypeptides encoded by the differentially expressed genes can also be isolated using conventional techniques such as affinity chromatography. For example, polyclonal or monoclonal antibodies can be raised against the polypeptide of interest and attached to a suitable affinity column by well-known techniques. See, e.g., Hudson & Hay, *Practical Immunology* (Blackwell Scientific Publications, Oxford, UK, 1980), Chapter 8 (incorporated by reference in its entirety). Peptide fragments can be generated from intact polypeptides by chemical or enzymatic cleavage methods known to those of skill in the art.

3. Other Methods

Alternatively, the polypeptides encoded by differentially expressed genes or gene fragments can be synthesized by chemical methods or produced by in vitro translation systems using a polynucleotide template to direct translation. Methods for chemical synthesis of polypeptides and in vitro translation are well-known in the art, and are described further by Berger & Kimmel, *Methods in Enzymology, Volume* 152, *Guide to Molecular Cloning Techniques*, Academic Press, Inc., San Diego, Calif., 1987 (incorporated by reference in its entirety).

C. Utility

The polypeptides can be used to generate antibodies that specifically bind to epitopes associated with the polypeptides or fragments thereof. Commercially available computer sequence analysis can be used to determine the location of the predicted major antigenic determinant epitopes of the polypeptide (e.g., MacVector from IBI, New Haven, Conn.). Once such an analysis has been performed, polypeptides can be prepared that contain at least the essential structural features of the antigenic determinant and can be utilized in the production of antisera against the polypeptide. Minigenes or gene fusions encoding these determinants can be constructed and inserted into expression vectors such as those described above using standard techniques. The major antigenic determinants can also be determined empirically in which portions of the gene encoding the polypeptide are expressed in a recombinant host, and the resulting proteins tested for their ability to elicit an immune response. For example, PCR can be used to prepare a range of cDNAs encoding polypeptides lacking successively longer fragments of the C-terminus of the polypeptide. The immunoprotective activity of each of these polypeptides then identifies those fragments or domains of the polypeptide that are essential for this activity. Further experiments in which only a small number or amino acids are removed at each iteration then allows the location of the antigenic determinants of the polypeptide.

Polypeptides encoded by target genes can be utilized in the development of pharmaceutical compositions, for example that modulate gene products associated cancerous cells. The process for identifying such polypeptides and subsequent compound development is described further below.

VI. Exemplary Screening, Diagnostic and Classification Methods

A. General Considerations

Certain methods that are provided involve determining the expression level of one or more of the differentially expressed genes in a test cell population with the expression level of the same genes in a control cell population, or comparing the expression profile for one sample with an expression profile determined for another sample. The level of expression of the differentially expressed nucleic acids can be determined at either the nucleic acid level or the protein level. Thus, the phrase "determining the expression level," "preparing a gene expression profile," and other like phrases when used in reference to the differentially expressed nucleic acids means that transcript levels and/or levels of protein encoded by the differentially encoded nucleic acids are detected. When determining the level of expression, the level can be determined qualitatively, but generally is determined quantitatively.

Based upon the sequence information that is disclosed herein, coupled with the nucleic acid and protein detection methods that are described herein and that are known in the art, expression levels of these genes can readily determined. If transcript levels are determined, they can be determined using routine methods. For instance, the sequence information provided herein (e.g., GenBank sequence entries) can be used to construct nucleic acid probes using conventional methods such as various hybridization detection methods (e.g., Northern blots). Alternatively, the provided sequence information can be used to generate primers that in turn are used to amplify and detect differentially expressed nucleic acids that are present in a sample (e.g., quantitative RT-PCR methods). If instead expression is detected at the protein level, encoded protein can be detected and optionally quantified using any of a number of established techniques. One common approach is to use antibodies that specifically bind to the protein product in immunoassay methods. Additional details regarding methods of conducting differential gene expression are provided infra.

Expression levels can be detected for one, some, or all of the differentially expressed nucleic acids that are listed in one or more of the tables. With some methods, the expression levels for only 1, 2, 3, 4 or 5 differentially expressed nucleic acids are determined. In other methods, expression levels for at least 6, 7, 8, 9 or 10 differentially expressed nucleic acids are determined. In still other methods, expression levels for at least 15, 20, 25, 30, 35, 40, 45, 50, 55, or 60 differentially expressed nucleic acids are determined. In yet other methods, all of the differentially expressed genes in one or more of the tables are determined.

Determination of expression levels is typically done with a test sample taken from a test cell population. As used herein, the term "population" when used in reference to a cell can mean a single cell, but typically refers to a plurality of cells (e.g., a tissue sample). Certain screening methods are performed with test cells that are "capable of expressing" one or more of the differentially expressed nucleic acids. As used in this context, the phrase "capable or expressing" means that the gene of interest is in intact form and can be expressed within the cell.

A number of the methods that are provided involve a comparison of expression levels for certain differentially expressed nucleic acids in a "test cell" with the expression levels for the same nucleic acids in a "control cell" (also sometimes referred to as a "control sample," a "reference cell," a "reference value," or simply a "control"). Other methods involve a comparison between one expression profile and a baseline expression profile. In either case, the expression level for the control cell or baseline expression profile essentially establishes a baseline against which an experimental value is compared. The comparison of expression levels are meant to be interpreted broadly with respect to what is meant by: 1) the term "cell", 2) the time at which the expression levels for test and control cells are determined, and 3) with respect to the measure of the expression levels.

So, for example, although the term "test cell" and "control cell" is used for convenience, the term "cell" is meant to be construed broadly. A cell, for instance, can also refer to a population of cells (e.g., a tissue sample), just as a population of cells can have a single member. The cell may in some instances be a sample that is derived from a cell (e.g., a cell lysate, a homogenate, or a cell fraction). In general samples can be obtained from various sources, particularly sources of lymphocytes.

With respect to timing, comparison of expression levels can be done contemporaneously (e.g., a test and control cell are each contacted with a test agent in parallel reactions). The comparison alternatively can be conducted with expression levels that have been determined at temporally distinct times. As an example, expression levels for the control cell can be collected prior to the expression levels for the test cell and stored for future use (e.g., expression levels stored on a computer compatible storage medium).

The expression level for a control cell or baseline expression profile (e.g., baseline value) can be a value for a single cell or it can be an average, mean or other statistical value determined for a plurality of cells. As an example, the expression level for a control cell can be the average of the expression levels for a population of subjects (e.g., subjects not having an immune-related disorder such as asthma). In other instances, the value for each expression level for the control cell is a range of values representative of the range observed for a particular population. Expression level values can also be either qualitative or quantitative. The values for expression levels can also optionally be normalized with respect to the expression level of a nucleic acid that is not one of the markers under analysis.

The comparative analysis required in some methods involves determining whether the expression level values are "comparable" (or similar"), or "differ" from one another. In some instances, the expression levels for a particular marker in test and control cells are considered similar if they differ from one another by no more than the level of experimental error. Often, however, expression levels are considered similar if the level in the test cell differs by less than 5%, 10%, 20%, 50%, 100%, 150%, or 200% with respect to the control cell. It thus follows that in some instances the expression level for a particular marker in the test cell is considered to differ from the expression level for the same marker in the control cell if the difference is greater than the level of experimental error, or if it is greater than 5%, 10%, 20%, 50%, 100%, 150% or 200%. In some methods, the comparison involves a determination of whether there is a "statistically significant difference" in the expression level for a marker in the test and control cells. A difference is generally considered to be "statistically significant" if the probability of the observed difference occurring by chance (the p-value) is less than some predetermined level. As used herein a "statistically significant difference" refers to a p-value that is $<0.05$, preferably $<0.01$ and most preferably $<0.001$. If gene expression is increased sufficiently such that it is different (as just defined) relative to the control cell or baseline, the expression of that gene is considered "up-regulated" or "increased." If, instead, gene expression is decreased so it differs from the control cell or baseline value, the expression of that gene is "down-regulated" or "decreased."

Comparison of the expression levels between test and control cells can involve comparing levels for a single marker or a plurality of markers (e.g., when expression profiles are compared). When the expression level for a single marker is determined, whether expression levels between the test and control cell are similar or different involves a comparison of the expression level of the single marker. When, however, expression levels for multiple markers are compared, the comparison analysis can involve two analyses: 1) a determination for each marker examined whether the expression level is similar between the test and control cells, and 2) a determination of how many markers from the group of markers examined show similar or different expression levels. The first determination is done as just described. The second determination typically involves determining whether at least 50% of the markers examined show similarity in expression levels. However, in methods were more stringent correlations are required, at least 60%, 70%, 80%, 90%, 95% or 100% of the markers must show similar expression levels for the expression levels of the group of markers examined considered to be similar between the test and control cells.

B. Screening Methods

1. Exemplary Approaches

Monitoring changes in gene expression can provide certain advantages during drug screening and development. Often drugs are pre-screened for the ability to interact with a major target without regard to other effects the drugs have on cells. Often such other effects cause toxicity in the whole animal, which prevent the development and use of the potential drug. These global changes in gene expression provide useful markers for diagnostic uses as well as markers that can be used to monitor disease states, disease progression, and drug metabolism. Thus, these expression profiles of genes provide molecular tools for evaluating drug toxicity, drug efficacy, and disease monitoring.

Changes in the expression profile from a baseline profile (e.g., the data in Table 1) can be used as an indication of such effects. Those skilled in the art can use any of a variety of known techniques to evaluate the expression of one or more of the genes and/or gene fragments identified in the present application in order to observe changes in the expression profile in a cell or sample of interest. Comparison of the expression data, as well as available sequence or other information may be done by researcher or diagnostician or may be done with the aid of a computer and databases.

In some screening methods, compounds and molecules are screened to identify those that affect expression of a target gene or some other gene involved in regulating the expression of a target gene (e.g., by interacting with the regulatory region or transcription factors of a target gene). Compounds are also screened to identify those that affect the activity of such proteins (e.g., by inhibiting target gene activity) or the activity of a molecule involved in the regulation of a target gene.

So, for example, in some methods potential drug compounds are screened to determine if application of the compound alters the expression of one or more of the target genes identified herein. This may be useful, for example, in determining whether a particular compound is effective in treating asthma or other immune-mediated disease. In the case in which the expression of a gene during the CD4+ lymphocyte polarization is affected by the potential drug compound, the compound is indicated in the treatment of asthma or other immune-mediated disease. Similarly, a drug compound which causes expression of a gene which is normally down-regulated during the CD4+ lymphocyte polarization, may be indicated in the treatment of the same diseases.

According to the present invention, the target genes listed in Table 2, 3, 5, 6, and/or 7 may also be used as markers to evaluate the effects of a candidate drug or agent on a lymphocyte cell, particularly undergoing polarization. A candidate drug or agent can be screened for the ability to stimulate the transcription or expression of a given marker or markers (drug targets) or to down-regulate or inhibit the transcription or expression of a marker or markers. According to the present invention, one can also compare the specificity of a drug's effects by looking at the number of markers affected by the drug and comparing them to the number of markers affected by a different drug. A more specific drug will affect fewer transcriptional targets. Similar sets of markers identified for two drugs indicates a similarity in effect.

Some method are designed for identifying agents that modulate the levels, concentration or at least one activity of a protein(s) encoded by one or several genes in Table 2, 3, 5, 6, and/or 7. Such methods or assays may utilize any means of monitoring or detecting the desired activity.

One specific embodiment of the invention is a method of identifying a compound capable of modulating the polarization of CD4+ lymphocytes, the method comprising:

(a) contacting the compound with naïve CD4+ lymphocytes;
(b) inducing the polarization of the lymphocytes;
(c) preparing a gene expression profile from the lymphocytes;
(d) comparing the lymphocyte gene expression profile to a gene expression profile derived from Table 2, 3, 5, 6, and/or 7.

Preferably the induction of step (b) is performed by contacting the lymphocytes with a cytokine. Preferably the cytokine is IL-12 or IL-4. A difference in the expression profiles of the target genes identifies a potential drug compound for the treatment of asthma or other immune-mediated diseases. Another preferred embodiment of the invention is an identification method of the invention, wherein said gene expression profile derived from Table 2, 3, 5, 6, and/or 7 is at least partly based on the expression fold changes of any one of the genes selected from the group consisting of: AW629527, AI969697, AI610684, AW152437, AW139719, R14890, AA489100, MGC16044, CGI-72, ZNF443, RAB30, NDFIP2, CD47, AMICA, CISH, SOCS3, ELL2, FOSL2, RNF19, RNF125, ZBED2, SYTL3, SLC37A3, AA002140, AA237039, LOC285628, PALM2, DACT1, VMP1, and ATP6V0A2.

Assays and screens can be used to identify compounds that are effective activators or inhibitors of target gene expression or activity. The assays and screens can be done by physical selection of molecules from libraries, and computer comparisons of digital models of compounds in molecular libraries and a digital model of the active site of the target gene product (i.e., protein).

The activators or inhibitors identified in the assays and screens may act by, but are not limited to, binding to a target gene product, binding to intracellular proteins that bind to a target gene product, compounds that interfere with the interaction between a target gene product and its substrates, compounds that modulate the activity of a target gene, or compounds that modulate the expression of a target gene or a target gene product.

Assays can also be used to identify molecules that bind to target gene regulatory sequences (e.g., promoter sequences), thus modulating gene expression. See, e.g., Platt (1994), J. Biol. Chem., 269:28558-28562.

Another specific embodiment of the invention is a method of identifying a compound that modulates the expression of at least one gene listed in Table 2, 3, 5, 6, and/or 7. These methods involve:

(a) incubating a cell that can express a protein from the gene with a compound under conditions and for a time sufficient for the cell to express the protein of said gene, when the compound is not present;
(b) incubating a control cell under the same conditions and for the same time without the compound;
(c) measuring expression of the gene in the cell in the presence of the compound;
(d) measuring expression of the gene in the control cell; and
(e) comparing the amount of expression of the gene in the presence and absence of the compound, wherein a difference in the level of expression indicates that the compound modulates the expression of the gene.

Another specific embodiment of the invention is a method of identifying a compound that modulates the activity of at least one gene listed in Table 2 or Table 6, the method comprising:
(a) incubating a cell that has said activity with a compound under conditions and for a time sufficient for the cell to express said activity, when the compound is not present;
(b) incubating a control cell under the same conditions and for the same time without the compound;
(c) measuring said activity in the cell in the presence of the compound;
(d) measuring said activity in the control cell; and
(e) comparing the amount of said activity in the presence and absence of the compound, wherein a difference in the level of expression indicates that the compound modulates the activity of said gene.

In one preferred embodiment, the gene or genes is/are selected from the group consisting of: AW629527, AI969697, AI610684, AW152437, AW139719, R14890, AA489100, MGC16044, CGI-72, ZNF443, RAB30, NDFIP2, CD47, AMICA, CISH, SOCS3, ELL2, FOSL2, RNF19, RNF125, ZBED2, SYTL3, SLC37A3, AA002140, AA237039, LOC285628, PALM2, DACT1, VMP1, and ATP6V0A2.

Certain screening methods are performed with mouse lymphocytes. As an example, some methods involve identifying a compound capable of modulating the polarization of murine CD4+ lymphocytes. These methods comprise:
(a) contacting the compound with naïve murine CD4+ lymphocytes;
(b) inducing the polarization of the lymphocytes;
(c) preparing a gene expression profile from the lymphocytes; and
(d) comparing the lymphocyte gene expression profile to a gene expression profile derived from Table 2, 3, 5, 6, and/or 7.

This method can also be used for determining or confirming the activity of a compound in murine cells, when said compound is already identified in any one of the above-mentioned human lymphocyte assay based identification methods as a modulator for polarization of human lymphocytes.

2. Methods for Detecting Differential Gene Expression

Assays to monitor the expression of a marker or markers as defined in Table 2, 3, 5, 6, and/or 7 may utilize any available means of monitoring for changes in the expression level of the target genes. As used herein, an agent is said to modulate the expression of a target gene if it is capable of up- or down-regulating expression of the target gene in a lymphocyte cell during polarization. The protein products encoded by the genes identified herein can also be assayed to determine the amount of expression. Any method for specifically and quantitatively measuring a specific protein or mRNA or DNA product can be used. However, methods and assays of the invention typically utilize PCR or array or chip hybridization-based methods when seeking to detect the expression of a large number of genes.

The genes identified as being differentially expressed in lymphocytes may be used in a variety of nucleic acid detection assays to detect or quantify the expression level of a gene or multiple genes in a given sample. For example, traditional Northern blotting, dot blots, nuclease protection, RT-PCR, differential display methods, subtractive hybridization, and in situ hybridization may be used for detecting gene expression levels. Levels of mRNA expression may be monitored directly by hybridization of probes to the nucleic acids of the invention. Cell lines are exposed to an agent to be tested under appropriate conditions and time and total RNA or mRNA is isolated by standard procedures such those disclosed in Sambrook et al, Molecular Cloning—A Laboratory Manual, Cold Spring Harbor Laboratory Press, Cold Spring Harbor, N.Y. (1989).

One of skill in the art will appreciate that an enormous number of array designs are suitable for the practice of this invention. The high density array will typically include a number of probes that specifically hybridize to the sequences of interest. See WO 99/32660 for methods of producing probes for a given gene or genes. In addition, in a preferred embodiment, the array will include one or more control probes.

3. Exemplary Candidate Agents

Agents that are assayed in the above methods can be randomly selected or rationally selected or designed. As used herein, an agent is said to be randomly selected when the agent is chosen randomly without considering the specific sequences of the protein itself or those sequences involve din the interaction of the protein with its substrates or ligands, for instance. An example of randomly selected agents is a chemical library or a peptide combinatorial library, or a growth broth of an organism. As used herein, an agent is said to be rationally selected or designed when the agent is chosen on a nonrandom basis, taking into account the sequence of the target site and/or its conformation in connection with the agents action. Agents can be selected or designed by utilizing the peptide sequences that make up these sites. For example, a rationally selected peptide agent can be a peptide whose amino acid sequence is identical to or a derivative of any functional consensus site.

The agents of the present invention can be, as examples, peptides, small chemical molecules, vitamin derivatives, as well as carbohydrates, lipids, oligonucleotides and covalent and non-covalent combinations thereof. Dominant negative proteins, DNA encoding these proteins, antibodies to these proteins, peptide fragments of these proteins or mimics of these proteins may be introduced into cells. A "mimetic" as used herein refers to a protein having a modification of a region or several regions such that the protein mimetic has a structure chemically different from the parent peptide but topographically and functionally similar to the parent peptide. A skilled artisan can readily recognize that there is no limit as to the structural nature of the agents of the present invention.

Some compounds are peptides, including but not limited to, soluble peptides, including but not limited to members of random peptide libraries (see, e.g., Lam et al. (1991) Nature 354:82-84; Houghten et al. (1991) Nature 354:84-86), and combinatorial chemistry-derived molecular libraries made of D- and/or L-amino acids, phosphopeptides (including, but not limited to, members of random or partially degenerate, directed phosphopeptide libraries; see, e.g., Songyang et al. (1993) Cell 72:767-778), and small organic or inorganic molecules.

3. Computerized Analysis

Computer modeling or searching technologies can be used to identify compounds, or identify modified compounds that modulate or are candidates to modulate the expression or activity of a target gene product. For example, compounds likely to interact with the active site of the target gene product may be identified. The active site of target gene product can be identified using methods known in the art including, for example, analysis of the amino acid sequence of a molecule, and from a study of complexes formed by a target gene product with a native ligand. Chemical or X-ray crystallographic methods can be used to identify the active site of target gene product through the location of a bound ligand.

The three-dimensional structure of the active site can be determined. This can be done using known methods, including X-ray crystallography, which can be used to determine a complete molecular structure. Solid or liquid phase NMR can be used to determine certain intramolecular distances. Other methods of structural analysis can be used to determine partial or complete geometrical structures.

Computer-based numerical modeling can be used to complete an incomplete or insufficiently accurate structure. Modeling methods that can be used are, for example, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected from force fields known in physical chemistry. Information on incomplete or less accurate structures determined in this way can be incorporated as constraints on the structures computed by these modeling methods.

Having determined the structure of the active site of a target gene product, either experimentally, by modeling, or by a combination of methods, additional candidate modulating compounds can be identified by searching databases containing compounds along with information on their molecular structure. The compounds identified in such a search are those that have structures that match the active site structure, fit into the active site, or interact with groups defining the active site. The compounds identified by the search are potential target gene product modulating compounds.

These methods may also be used to identify improved modulating compounds from an already known modulating compounds or ligands. The structure of the known compound is modified and effects are determined using experimental and computer modeling methods. The altered structure is compared to the active site structure of a target gene product to determine or predict how a particular modification to the ligand or modulating compound will affect its interaction with that protein. Systematic variations in composition, such as by varying side groups, can be evaluated to obtain modified modulating compounds or ligands of preferred specificity or activity.

Given the teachings herein, additional experimental and computer modeling methods useful to identify modulating compounds based on identification of the active sites of a target gene product and related transduction and transcription factors can be developed by those skilled in the art. Computer programs designed to screen and depict chemicals as well as molecular modeling systems are available from companies such as MSI (Molecular Simulations, Inc., San Diego, Calif., USA), Allelix, Inc. (Mississauga, Ontario, Canada), and Hypercube, Inc. (Gainesville, Fla., USA).

In addition to designing and generating compounds that alter binding, as described above, libraries of known compounds, including natural products, synthetic chemicals, and biologically active materials including peptides, can be screened for compounds that are inhibitors or activators.

Compounds identified by methods described above may be useful, for example, for elaborating the biological function of target gene products and in treatment of disorders in which target gene activity is deleterious.

C. Diagnostic Methods

Methods for assessing whether a subject has or is predisposed to obtain an immune-mediated disease (e.g. asthma, allergy or auto-immune disease) are also provided. These methods generally involve obtaining a sample from a subject having or suspected to have an immune-mediated disease. The expression levels for one or more the differentially expressed genes is then determined for the sample. The population of test cells is selected to include lymphocytic cells from the subject.

The expression level of the gene(s) is then compared with the expression level of the same gene(s) in a control sample. The status of the control sample with respect to presence or absence of an immune-mediated disease is known (e.g., the control sample is from an individual not suffering from the immune-related disease of interest or is from an individual having an immune-related disease). So, for example, if the control cell is representative of cells from a healthy individual, then similarity in expression level or expression profile between the test and control samples indicates that the subject does not have an immune-related disease. A difference in expression level or profile, in contrast, indicates that the subject from whom the test sample was derived has an immune-related disease.

If instead, the control sample is representative of cells from an individual that has a particular immune-related disease, then similarity in expression levels or expression profile means that the test cells are from a patient that has, or is susceptible to, the immune-related disease; whereas, a difference in expression levels or profile indicates that the subject does not have the immune-related disease.

D. Classifying Lymphocytes

Other methods that are provided are designed to classify a lymphocyte or to assess its cellular state. Such methods generally involve obtaining a test sample derived from a lymphocyte that is capable of expressing one or more nucleic acid markers from the group consisting of those listed in one or more of the tables (e.g., Table 1, or Table 2 or Table 6. The expression level for one or more of these markers is then determined. The expression level for these markers is compared with the expression levels of the same markers in a control sample. The control sample is derived from a lymphocytic cell whose cellular status is known (e.g., the cell is known to be a Th1 or Th2 cell). The lymphocytic cell from which the test sample is derived is then classified on the basis of this comparison.

For example, if the expression level or expression profile of the test sample is compared with expression levels or an expression profile from a Th1 cell, similarity in expression profile is an indication that the lymphocyte from which the test sample is derived is a Th1 cell. A difference, on the other hand, would be an indication that the sample is from a lymphocyte of another type or in another state (e.g., a Th2 cell).

VII. Treatment Methods

Methods of treating a patient with asthma or other immune-mediated diseases are also provided. These methods generally involve administering to the patient a pharmaceutical composition, wherein the composition alters the expression or activity of at least one gene listed in Table 2, 3, 5, 6, and/or 7. In a preferred embodiment, the active compound of the pharmaceutical composition is identified by a screening method of the invention. In another preferred embodiment, the active compound of said pharmaceutical composition is an antibody binding to at least one gene product of the genes listed in Table 2, 3, 5, 6, and/or 7.

Both therapeutic and prophylactic methods are provided. In therapeutic methods, a pharmaceutical composition is administered to a subject having or suspected to have an immune-related disease in an amount sufficient to alleviate one or more symptoms of the disease. In prophylactic methods, a pharmaceutical composition is administered to a subject susceptible to, or otherwise at risk for developing an immune-related disease, in an amount sufficient to reduce or arrest the development of the disease. The treatment can be administered in a single dose, but more commonly is administered in several doses.

If the immune-related disease, is a consequence of an excessive Th1 response, then certain methods involve administering an agent that inhibits the expression of a gene that is up-regulated during Th1 polarization or that inhibits the activity of the protein it encodes. Alternatively, an agent can be administered that activates the expression of a gene that is up-regulated in Th2 cells, or which increases the activity of the protein encoded by such a gene. A third option is to administer one or more agents that achieve both of these results.

If instead the disease is associated with an excessive Th2 response, then some treatment strategies involve administering an agent that inhibits the expression or activity of a gene that is up-regulated in Th2 cells. Alternatively, an agent is administered that activates the expression or activity of a gene that is up-regulated in Th1 cells. Still other methods involve providing an agent or agents that accomplishes both of these results.

A number of methods that are known in the art can be utilized to modulate gene expression or activity. Various agents can be used to inhibit gene expression or the activity of the corresponding protein. Examples of such agents include antisense oligonucleotides, ribozymes, triple helix structure and double-stranded RNA (dsRNA), particularly small-interfering RNAs (siRNAs). These agents are discussed in additional detail below. Alternatively, compounds that antagonize the activity of the protein encoded by the up-regulated genes can also be utilized. Examples include antibodies that specifically bind to the encoded protein. Other antagonists are small molecules.

Various options are also available for increasing gene expression or the activity of the protein encoded by a gene. One option is to administer a nucleic acid that encodes the protein whose activity one seeks to increase. This nucleic acid is operably linked to an appropriate expression control elements to facilitate its expression lymphocytes. Another option is to administer the protein itself, or an active fragment thereof. Yet another option is to administer an agonist that increases the activity of the protein.

VIII. Compounds for Inhibiting or Enhancing the Synthesis or Activity of Control Genes A. Activity or Synthesis Inhibition As discussed above, expression of certain genes can cause or worsen the symptoms of an immune-related disease. The increase in the expression or activity of such control genes and their products can be countered using various methodologies to inhibit their expression, synthesis or activity.

For example, antisense, ribozyme, triple helix molecules and antibodies can be utilized to ameliorate the negative effects of such control genes and gene products. Antisense RNA and DNA molecules act directly to block the translation of mRNA by hybridizing to targeted mRNA, thereby blocking protein translation. Hence, a useful target for antisense molecules is the translation initiation region.

Ribozymes are enzymatic RNA molecules that hybridize to specific sequences and then carry out a specific endonucleolytic cleavage reaction. Thus, for effective use, the ribozyme should include sequences that are complementary to the target mRNA, as well as the sequence necessary for carrying the cleavage reaction (see, e.g., U.S. Pat. No. 5,093,246).

Nucleic acids utilized to promote triple helix formation to inhibit transcription are single-stranded and composed of dideoxyribonucleotides. The base composition of such polynucleotides is designed to promote triple helix formation via Hoogsteen base pairing rules and typically require significant stretches of either pyrimidines or purines on one strand of a duplex.

Double stranded RNA (dsRNA) inhibition methods can also be use to inhibit expression of one or more of the differentially expressed nucleic acids. The RNA utilized in such methods is designed such that a least a region of the dsRNA is substantially identical to a region of a differentially expressed nucleic acid (e.g., a target gene); in some instances, the region is 100% identical to the target. For use in mammals, the dsRNA is typically about 19-30 nucleotides in length (i.e., small inhibitory RNAs are utilized (siRNA)). Methods and compositions useful for performing dsRNAi and siRNA are discussed, for example, in PCT Publications WO 98/53083; WO 99/32619; WO 99/53050; WO 00/44914; WO 01/36646; WO 01/75164; WO 02/44321; and published U.S. patent application Ser. No. 10/195,034, each of which is incorporated herein by reference in its entirety for all purposes.

Antibodies having binding specificity for a target gene protein that also interferes with the activity of the gene protein can also be utilized to inhibit gene protein activity. Such antibodies can be generated from full-length proteins or fragments thereof according to the methods described below.

B. Activity Enhancement

Immune-related diseases can be exacerbated by under-expression of certain control genes and/or by a reduction in activity of a control gene product, for example. Alternatively, the up-regulation of certain control gene products can produce a beneficial effect. In any of these scenarios, it is useful to increase the expression, synthesis or activity of such control genes and proteins.

These goals can be achieved, for example, by increasing the level of control gene product or the concentration of active gene product. In one approach, a control gene protein in the form of a pharmaceutical composition such as that described below is administered to a subject suffering from an immune-related disease. Alternatively, DNA sequences encoding control gene proteins can be administered to a patient at a concentration sufficient to treat a immune-related disease or to treat an individual at risk for such a disease. Gene therapy is yet another option and includes inserting one or more copies of a normal control gene, or a fragment thereof capable of producing a functional control protein, into lymphocytic cells using various vectors. Suitable vectors include, for example, adenovirus, adeno-associated virus and retrovirus vectors. Liposomes and other particles capable of introducing DNA into cells can also be utilized in some instances. Cells, typically autologous cells, that express a normal control gene can than be introduced or reintroduced into a patient to treat the immune-related disease.

X. Antibodies

Antibodies that are immunoreactive with polypeptides expressed from the differentially expressed genes or fragments thereof are also provided. The antibodies can be polyclonal antibodies, distinct monoclonal antibodies or pooled monoclonal antibodies with different epitopic specificities.

A. Production of Antibodies

The antibodies can be prepared using intact polypeptide or fragments containing antigenic determinants from proteins encoded by differentially expressed genes or target genes as the immunizing antigen. The polypeptide used to immunize an animal can be from natural sources, derived from translated cDNA, or prepared by chemical synthesis. In some instances the polypeptide is conjugated with a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). Various adjuvants can be utilized to increase the immunological response, depending on the host species and include, but are not limited to, Freund's (complete and incomplete), mineral gels such as aluminum hydroxide, surface active substances such as lysolecithin, pluronic polyols, polyanions, peptides, oil emulsions, dinitrophenol and carrier proteins, as well as human adjuvants such as BCG (bacille Calmette-Guerin) and *Corynebacterium parvum*.

Monoclonal antibodies can be made from antigen-containing fragments of the protein by the hybridoma technique, for example, of Kohler and Milstein (Nature, 256:495-497, (1975); and U.S. Pat. No. 4,376,110, incorporated by reference in their entirety). See also, Harlow & Lane, *Antibodies, A Laboratory Manual* (C.S.H.P., NY, 1988), incorporated by reference in its entirety. The antibodies can be of any immunoglobulin class including IgG, IgM, IgE, IgA, IgD and any subclass thereof.

Techniques for generation of human monoclonal antibodies have also been described, including, for example, the human B-cell hybridoma technique (Kosbor et al., *Immunology Today* 4:72 (1983), incorporated by reference in its entirety); for a review, see also, Larrick et al., U.S. Pat. No. 5,001,065, (incorporated by reference in its entirety). An alternative approach is the generation of humanized antibodies by linking the complementarity-determining regions or CDR regions (see, e.g., Kabat et al., "Sequences of Proteins of Immunological Interest," U.S. Dept. of Health and Human Services, (1987); and Chothia et al., *J. Mol. Biol.* 196:901-917 (1987)) of non-human antibodies to human constant regions by recombinant DNA techniques. See Queen et al., *Proc. Natl. Acad. Sci. USA* 86:10029-10033 (1989) and WO 90/07861 (incorporated by reference in its entirety). Alternatively, one can isolate DNA sequences that encode a human monoclonal antibody or a binding fragment thereof by screening a DNA library from human B cells according to the general protocol set forth by Huse et al., *Science* 246:1275-1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047 (each of which is incorporated by reference). Phage display technology can also be used to mutagenize CDR regions of antibodies previously shown to have affinity for the peptides of the present invention. Antibodies having improved binding affinity are selected.

Techniques developed for the production of "chimeric antibodies" by splicing the genes from a mouse antibody molecule of appropriate antigen specificity together with genes from human antibody molecule of appropriate antigen specificity can be used. A chimeric antibody is a molecule in which different portions are derived from different species, such as those having a variable region derived from a murine monoclonal antibody and a human immunoglobulin constant region. Single chain antibodies specific for the differentially expressed gene products of the invention can be produced according to established methodologies (see, e.g., U.S. Pat. No. 4,946,778; Bird, *Science* 242:423-426 (1988); Huston et al., *Proc. Natl. Acad. Sci. USA* 85:5879-5883 (1988); and Ward et al., *Nature* 334:544-546 (1989), each of which is incorporated by reference in its entirety). Single chain antibodies are formed by linking the heavy and light chain fragments of the Fv region via an amino acid bridge, resulting in a single chain polypeptide.

Antibodies can be further purified, for example, by binding to and elution from a support to which the polypeptide or a peptide to which the antibodies were raised is bound. A variety of other techniques known in the art can also be used to purify polyclonal or monoclonal antibodies (see, e.g., Coligan, et al., Unit 9, *Current Protocols in Immunology*, Wiley Interscience, (1994), incorporated herein by reference in its entirety).

Anti-idiotype technology can also be utilized in some instances to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody.

B. Use of Antibodies

The antibodies that are provided are useful, for example, in screening cDNA expression libraries and for identifying clones containing cDNA inserts which encode structurally-related, immunocrossreactive proteins. See, for example, Aruffo & Seed, *Proc. Natl. Acad. Sci. USA* 84:8573-8577 (1977) (incorporated by reference in its entirety). Antibodies are also useful to identify and/or purify immunocrossreactive proteins that are structurally related to native polypeptide or to fragments thereof used to generate the antibody. The antibodies can also be used to form antibody arrays to detect proteins expressed by the differentially expressed genes.

The antibodies can also be used in the detection of differentially expressed genes, such as control and fingerprint gene products. Various diagnostic assays can be utilized, including but not limited to, competitive binding assays, direct or indirect sandwich assays and immunoprecipitation assays (see, e.g., *Monoclonal Antibodies: A Manual of Techniques*, CRC Press, Inc. (1987) pp. 147-158). When utilized in diagnostic assays, the antibodies are typically labeled with a detectable moiety. The label can be any molecule capable of producing, either directly or indirectly, a detectable signal. Suitable labels include, for example, radioisotopes (e.g., $^3$H, $^{14}$C, $^{32}$P, $^{35}$S, $^{125}$I), fluorophores (e.g., fluorescein and rhodamine dyes and derivatives thereof), chromophores, chemiluminescent molecules, an enzyme substrate (including the enzymes luciferase, alkaline phosphatase, beta-galactosidase and horse radish peroxidase, for example). The antibodies can also be utilized in the development of antibody arrays.

As noted above, antibodies are useful in inhibiting the expression products of the differentially expressed genes and are valuable in inhibiting the action of certain control gene products (e.g., target gene products identified as causing or exacerbating tumor or cancer formation). Hence, the antibodies also find utility in a variety of therapeutic applications.

XI. Pharmaceutical Compositions

The invention provides also a pharmaceutical composition that can modulate the expression or activity of at least one gene listed in one or more of the tables (e.g., Table 2 or Table 6) for use in prophylaxis or treatment of asthma or other immune-mediated disease. In a preferred embodiment said pharmaceutical composition comprises an antibody binding to at least one gene product of the genes listed in Table 2, 3, 5, 6, and/or 7 as an active ingredient.

A. Composition

The pharmaceutical compositions used for treatment of cancers and tumors comprise an active ingredient such as the inhibitory or activity-enhancing compounds such as described herein and, optionally, various other components.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like.

The composition can also include any of a variety of stabilizing agents, such as an antioxidant for example. When the pharmaceutical composition includes a polypeptide, the polypeptide can be complexed with various well known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include the production of sulfate, gluconate, citrate, phosphate and the like. The polypeptides of the composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in *Remington's Pharmaceutical Sciences*, Mace Publishing Company, Philadelphia, Pa., 17th ed. (1985). For a brief review of methods for drug delivery, see, Langer, *Science* 249:1527-1533 (1990).

B. Dosage

The pharmaceutical compositions can be administered for prophylactic and/or therapeutic treatments. The active ingredient in the pharmaceutical compositions typically is present in a therapeutic amount, which is an amount sufficient to slow or reverse tumor formation, to eliminate the tumor, or to remedy symptoms associated with the tumor or cancer. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

In prophylactic applications, compositions containing the compounds that are provided are administered to a patient susceptible to or otherwise at risk of tumor formation. Such an amount is defined to be a "prophylactically effective" amount or dose. In this use, the precise amount depends on the patient's state of health and weight. Typically, the dose ranges from about 1 to 500 mg of purified protein per kilogram of body weight, with dosages of from about 5 to 100 mg per kilogram being more commonly utilized.

C. Administration

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules, which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Formulations for injection can be presented in unit dosage form, e.g., in ampules or in multidose containers, with an added preservative. The compositions are formulated as sterile, substantially isotonic and in full compliance with all Good Manufacturing Practice (GMP) regulations of the U.S. Food and Drug Administration.

XII. Devices for Detecting Differentially Expressed Nucleic Acids

A. Customized Probe Arrays

1. Probes for Differentially Expressed Genes

The differentially expressed genes that are provided can be utilized to prepare custom probe arrays for use in screening and diagnostic applications. In general, such arrays include probes such as those described above in the section on differentially expressed nucleic acids, and thus include probes complementary to full-length differentially expressed nucleic acids (e.g., cDNA arrays) and shorter probes that are typically 10-30 nucleotides long (e.g., synthesized arrays). Typically, the arrays include probes capable of detecting a plurality of the differentially expressed genes of the invention. For example, such arrays generally include probes for detecting at least 2, 3, 4, 5, 6, 7, 8, 9 or 10 differentially expressed nucleic acids. For more complete analysis, the arrays can include probes for detecting at least 12, 14, 16, 18 or 20 differentially expressed nucleic acids. In still other instances, the arrays include probes for detecting at least 25, 30, 35, 40, 45 or all the differentially expressed nucleic acids that are identified herein.

2. Control Probes (a) Normalization Controls

Normalization control probes are typically perfectly complementary to one or more labeled reference polynucleotides that are added to the nucleic acid sample. The signals obtained from the normalization controls after hybridization provide a control for variations in hybridization conditions, label intensity, reading and analyzing efficiency and other factors that can cause the signal of a perfect hybridization to vary between arrays. Signals (e.g., fluorescence intensity) read from all other probes in the array can be divided by the signal (e.g., fluorescence intensity) from the control probes thereby normalizing the measurements.

Virtually any probe can serve as a normalization control. However, hybridization efficiency can vary with base composition and probe length. Normalization probes can be selected to reflect the average length of the other probes present in the array, however, they can also be selected to cover a range of lengths. The normalization control(s) can also be selected to reflect the (average) base composition of the other probes in the array. Normalization probes can be localized at any position in the array or at multiple positions throughout the array to control for spatial variation in hybridization efficiently.

(b) Mismatch Controls

Mismatch control probes can also be provided; such probes function as expression level controls or for normalization controls. Mismatch control probes are typically employed in customized arrays containing probes matched to known mRNA species. For example, certain arrays contain a mismatch probe corresponding to each match probe. The mismatch probe is the same as its corresponding match probe except for at least one position of mismatch. A mismatched base is a base selected so that it is not complementary to the corresponding base in the target sequence to which the probe can otherwise specifically hybridize. One or more mismatches are selected such that under appropriate hybridization conditions (e.g. stringent conditions) the test or control probe can be expected to hybridize with its target sequence, but the mismatch probe cannot hybridize (or can hybridize to a significantly lesser extent). Mismatch probes can contain a central mismatch. Thus, for example, where a probe is a 20 mer, a corresponding mismatch probe can have the identical sequence except for a single base mismatch (e.g., substituting a G, a C or a T for an A) at any of positions 6 through 14 (the central mismatch).

(c) Sample Preparation, Amplification, and Quantitation Controls

Arrays can also include sample preparation/amplification control probes. Such probes can be complementary to subsequences of control genes selected because they do not normally occur in the nucleic acids of the particular biological sample being assayed. Suitable sample preparation/amplification control probes can include, for example, probes to bacterial genes (e.g., Bio B) where the sample in question is a biological sample from a eukaryote.

The RNA sample can then be spiked with a known amount of the nucleic acid to which the sample preparation/amplification control probe is complementary before processing. Quantification of the hybridization of the sample preparation/amplification control probe provides a measure of alteration in the abundance of the nucleic acids caused by processing steps. Quantitation controls are similar. Typically, such controls involve combining a control nucleic acid with the sample nucleic acid(s) in a known amount prior to hybridization. They are useful to provide a quantitative reference and permit determination of a standard curve for quantifying hybridization amounts (concentrations).

3. Array Synthesis

Nucleic acid arrays for use in the present invention can be prepared in two general ways. One approach involves binding DNA from genomic or cDNA libraries to some type of solid support, such as glass for example. (See, e.g., Meier-Ewart, et al., *Nature* 361:375-376 (1993); Nguyen, C. et al., *Genomics* 29:207-216 (1995); Zhao, N. et al., *Gene*, 158:207-213 (1995); Takahashi, N., et al., *Gene* 164:219-227 (1995); Schena, et al., *Science* 270:467-470 (1995); Southern et al., *Nature Genetics Supplement* 21:5-9 (1999); and Cheung, et al., *Nature Genetics Supplement* 21:15-19 (1999), each of which is incorporated herein in its entirety for all purposes.)

The second general approach involves the synthesis of nucleic acid probes. One method involves synthesis of the probes according to standard automated techniques and then post-synthetic attachment of the probes to a support. See for example, Beaucage, *Tetrahedron Lett.*, 22:1859-1862 (1981) and Needham-VanDevanter, et al., *Nucleic Acids Res.*, 12:6159-6168 (1984), each of which is incorporated herein by reference in its entirety. A second broad category is the so-called "spatially directed" polynucleotide synthesis approach. Methods falling within this category further include, by way of illustration and not limitation, light-directed polynucleotide synthesis, microlithography, application by ink jet, microchannel deposition to specific locations and sequestration by physical barriers.

Light-directed combinatorial methods for preparing nucleic acid probes are described in U.S. Pat. Nos. 5,143,854 and 5,424,186 and 5,744,305; PCT patent publication Nos. WO 90/15070 and 92/10092; EP 476,014; Fodor et al., *Science* 251:767-777 (1991); Fodor, et al., *Nature* 364:555-556 (1993); and Lipshutz, et al., *Nature Genetics Supplement* 21:20-24 (1999), each of which is incorporated herein by reference in its entirety. These methods entail the use of light to direct the synthesis of polynucleotide probes in high-density, miniaturized arrays. Algorithms for the design of masks to reduce the number of synthesis cycles are described by Hubbel et al., U.S. Pat. Nos. 5,571,639 and 5,593,839, and by, Fodor et al., *Science* 251:767-777 (1991), each of which is incorporated herein by reference in its entirety.

Other combinatorial methods that can be used to prepare arrays for use in the current invention include spotting reagents on the support using ink jet printers. See Pease et al., EP 728, 520, and Blanchard, et al. *Biosensors and Bioelectronics* II: 687-690 (1996), which are incorporated herein by reference in their entirety. Arrays can also be synthesized utilizing combinatorial chemistry by utilizing mechanically constrained flowpaths or microchannels to deliver monomers to cells of a support. See Winkler et al., EP 624,059; WO 93/09668; and U.S. Pat. No. 5,885,837, each of which is incorporated herein by reference in its entirety.

4. Array Supports

Supports can be made of any of a number of materials that are capable of supporting a plurality of probes and compatible with the stringency wash solutions, Examples of suitable materials include, for example, glass, silica, plastic, nylon or nitrocellulose. Supports are generally are rigid and have a planar surface. Supports typically have from 1-10,000,000 discrete spatially addressable regions, or cells. Supports having 10-1,000,000 or 100-100,000 or 1000-100,000 regions are common. The density of cells is typically at least 1000, 10,000, 100,000 or 1,000,000 regions within a square centimeter. Each cell includes at least one probe; more frequently, the various cells include multiple probes. In general each cell contains a single type of probe, at least to the degree of purity obtainable by synthesis methods, although in other instances some or all of the cells include different types of probes. Further description of array design is set forth in WO 95/11995, EP 717,113 and WO 97/29212, which are incorporated by reference in their entirety.

XIII. Kits

Kits containing components necessary to conduct the screening and diagnostic methods of the invention are also provided. Some kits typically include a plurality of probes that hybridize under stringent conditions to the different differentially expressed nucleic acids that are provided. Other kits include a plurality of different primer pairs, each pair selected to effectively prime the amplification of a different differentially expressed nucleic acid. In the case when the kit includes probes for use in quantitative RT-PCR, the probes can be labeled with the requisite donor and acceptor dyes, or these can be included in the kit as separate components for use in preparing labeled probes.

The kits can also include enzymes for conducting amplification reactions such as various polymerases (e.g., RT and Taq), as well as deoxynucleotides and buffers. Cells capable of expressing one or more of the differentially expressed nucleic acids of the invention can also be included in certain kits.

Typically, the different components of the kit are stored in separate containers. Instructions for use of the components to conduct an analysis are also generally included.

The following examples are offered to illustrate certain aspects of the methods and devices that are provided; it should be understood that these examples are not to be construed to limit the claimed invention.

Experimental Section

Materials and Methods
In Vitro Differentiation of Th1 and Th2 cells.

Induction of human Th1 and Th2 cell differentiation was performed as previously described (10). Briefly, CD4+ T cells isolated (Ficol Isolation Paque, Amersham Pharmacia Biotech, Uppsala, Sweden and Dynal, Oslo, Norway) from cord blood (Turku University Central Hospital, Finland) were activated with plate-bound anti-CD3 (500-1000 ng/ml for coating) and 500 ng/ml of soluble anti-CD28 (both from Immunotech, Marseille, France). Th1 polarization was induced with 2.5 ng/ml of IL12 and Th2 differentiation with 10 ng/ml of IL4 (both from R&D Systems, Minneapolis, Minn.). Part of the cells was cultured in "neutral conditions" without polarizing cytokines. In the indicated experiments the cultures were supplemented with 3 ng/ml of TGFβ (R&D Systems). TGFβ-mediated suppression of IFNγ production by Th1 cells in these conditions is has been previously described (10). The samples were collected after 0, 2, 6, 24 or 48 h of polarization.

For validation of the oligonucleotide array results with Real-Time RT-PCR, additional Th1 and Th2 primary cultures were generated as previously described (11). Briefly, cord blood CD4+ T cells were activated with 100 ng/ml of PHA (Murex Diagnostics, Chatillon, France) and irradiated CD32-B7 transfected fibroblasts (15). Th1 cultures were supplemented with 2.5 ng/ml of IL12, whereas Th2 cultures were supplemented with 10 mg/ml of anti-IL12 and 10 ng/ml of IL4 (all from R&D Systems, Minneapolis, Minn.). After 48 h of priming, 40 U/ml of IL2 (R&D Systems) was added into the cultures. Part of the cells was cultured without any polarizing cytokines in the presence of IL2 alone. The cultures were generated from four individuals. Samples were collected at the time points of 0, 6, 24 and 48 h or 7 d.

Oligonucleotide Array Studies.

The samples previously prepared and hybridised to human U95Av2 arrays, were rehybridised on human genome U133A and B arrays containing approximately 33 000 probes for different genes (10), (unpublished data). Briefly, sample preparation and data analysis was performed according to the instructions and recommendations provided by the manufacturer (Affymetrix, Santa Clara, Calif.). Total RNA (4-5 µg) pooled from different individuals was used as starting material for the Affymetrix sample preparation. Two biological repeats for each microarray experiment were performed. GeneChip Microarray Suite software version 5 (MAS5, Affymetrix), GeneSpring (SiliconGenetics, Redwood, Calif.) and Microsoft access for Windows softwares were used for data analysis and processing. The normalized numerical data was filtered on four consecutive levels according to the statistical classifications performed by the MAS5 software based on 16 probes for each gene. At the detection level, all the genes that were assigned to be "absent" in both samples compared were removed. Similarly all the genes that were classified as "no change" were removed. Subsequently, the gene expression was considered to be up-regulated, if the signal log ratio between the reference and the target samples was higher than one (2-fold increase) and the target sample was "present". Similarly, a gene was defined as down-regulated, if the signal log ratio was less than minus one (2-fold decrease) and the reference sample was "present". At the fourth level of data analysis, genes that presented a consistent change in two separate biological repeats were considered as differentially expressed. All the genes, which fulfilled these criteria in at least one of the comparisons and one of the time points, were selected for further analysis where the expression of the genes was explored parallel in different conditions without fold change threshold. The gene annotations were obtained from NetAffx-database (16).

Real-Time Quantitative RT-PCR.

To validate the oligonucleotide array results for the selected genes Real-time quantitative RT-PCR (TaqMan ABI Prism 7700, Applied Biosystems, Foster City, Calif.) was performed as described before (11, 15). Housekeeping gene EF1α was used as a reference transcript (15). Primers and probes (Table I) used for the quantification of gene expression (MedProbe, Oslo, Norway) were designed using Primer Express software (Applied Biosystems).

Results

To identify novel genes involved in the initiation and early polarization of Th1 and Th2 cells at genome scale, Affymetrix U133A&B oligonucleotide arrays were used to study the changes in gene expression during the early polarization process. To identify the genes regulated by IL12 or IL4 in activated Th cells, the cells induced to polarize to Th1 (CD3+CD28+IL12) or Th2 (CD3+CD28+IL4) direction for 2, 6 or 48 h were compared to CD3+CD28-activated cells cultured without polarizing cytokines. To identify the genes differentially expressed in Th1 and Th2 condition, the cells induced to polarize to Th1 (CD3+CD28+IL12) or Th2 (CD3+CD28+IL4) were directly compared to each other. In addition to the previously identified genes, altogether 173 genes were identified to be differentially expressed in Th1 and Th2 polarizing conditions or to be regulated by the IL12 or IL4 during the first two days of Th1 and Th2 differentiation (17), (unpublished data).

Genes Regulated by IL12 During the Early Th1 Differentiation.

Concordant with our previous observations (unpublished data), IL12 had no or only minimal effect on the polarization process after 2 or 6 h. After 2 h of Th1 polarization, there were no genes regulated by IL12. After 6 h, less than 2-fold induction by IL12 was seen in the expression of key regulator of Th1 differentiation TBX21 and GTPase GBP5 (3, 4). After 48 h, the effects of IL12 were clear and altogether 40 genes become regulated by IL12 (Table II). Of these genes 29 were induced and 11 were repressed by IL12. Among these were only SOCS3, CEBPB and IL7R that have previously described role in Th1 and Th2 cell responses (13, 18, 19). A subset of the IL12-regulated genes were regulated to same direction by IL4 or CD3+CD28-activation alone, although for at least some of the genes, there was a difference in the magnitude of the change in response to different treatment.

This indicates that the effects of IL12 were not specific on these genes. For a subset of 14 of these genes the effects by IL12 were specific. Of these KIAA0992, JDP1, LOC83690, LOC340061, IL7R, HIMAP4, PBF and CRA CC were up-regulated and PPAP2A, MGC4677, PRG1, CRIP1, BE222344 and H99792 were down-regulated specifically by IL12. Of the 40 genes regulated by IL12 only 21 were differentially expressed during the early Th1 and Th2 cells differentiation.

Genes Regulated by IL4 During the Early Th2 Differentiation.

IL4 regulated expression of altogether 165 genes during the early Th2 differentiation. Of these 41 were down-regulated and 124 up-regulated. Only a few of these genes including CD47, PRNP, SOCS3, FOSL2, COL6A3, PTPRA, TNFSF10, IL10, CCR7, CEBPB, IL7R, GBP3 and TBX21 have been previously associated with Th1 and Th2 cell differentiation (3, 8, 12, 13, 18-22). Constant regulation by IL4 was seen for 48 genes that were regulated by IL4 in more than one time point (Table III). For the rest of the 117 genes regulation by IL4 was observed at only one of the time points studied (see supplementary material). As was observed for the IL12-regulated genes, some of the IL4 target genes were regulated to the same direction by IL12 or CD3+CD28-activation alone. However, for 90 genes (19 down-regulated and 71 up-regulated) the effects of IL4 were specific. Of the 165 IL4-regulated genes, altogether 133 were also differentially expressed between the cells induced to polarize to Th1 or Th2 direction.

In contrast to the IL12 signaling, the effects of IL4 were seen clearly already within 2 h of Th2 polarization, when altogether 62 genes become up-regulated by IL4. For 36 of these genes the upregulation by IL4 was detected in more than one time point. For the genes AI969697, NDFIP2, CD47, PALM2, CISH, VMP1, DACT1 and ELL2 the upregulation by IL4 was seen constantly at the all time points (2, 6 and 48 h). Only 9 genes were detected to be down-regulated by IL4 after 2 h (KAI1, HIMAP4, VAMP1, AI681671, AI654547, TMEPAI, PLP2, TNFSF14, GADD45A). For the genes KAI1, HIMAP4 and VAMP1 the repression continued after 6 h. At 6-h time point 31 additional genes become up-regulated by IL4. For 6 of these genes (SYTL3, FOSL2, RNF19, ZBED2, SLC37A3, AW629527) the upregulation was maintained for 48 h of Th2 polarization. After 6 h the inhibitory effects of IL4 become stronger as 24 genes become down-regulated. Of these genes LOC285628 was repressed also after 48 h. After 48 h, 32 additional genes become up-regulated by IL4 and 6 genes were repressed.

Genes Regulated by Both IL12 and IL4

A subset of the genes identified to be involved in early Th1 and Th2 cell differentiation were regulated by both IL12 and IL4. Altogether 17 genes (SOCS3, VMP1, NDFIP2, LOC284018, SYTL3, ZBED2, HOP, MICAL2, KLHL6, SURF4, MICAL2, CD7, AI042152, C20orf97, CEBPB, SLC2A3, LMNA) were up-regulated and 3 genes (LY9, WASPIP, FLJ37712) were down-regulated by both of these cytokines. However, genes including SOCS3, VMP1, NDFIP2, LOC284018, SYTL3, ZBED2, LMNA, LY9 and FLJ37712 were regulated by different kinetics of magnitude by these cytokines. Importantly, another subset of these genes, including HIMAP4, IL7R, PPAP2A, MGC4677, TBX21 and GBP5, were regulated in an opposite manner by IL12 and IL4 (FIG. 1).

Putative or Known Functions of the Genes Involved in the Early Th1 and Th2 Differentiation.

Concordant with our previous studies, most of the genes involved in the early differentiation of Th1 and Th2 cells are coding for factors involved in the signal transduction from cell surface to nucleus (Table IV) (10), (unpublished data). The predominant functional groups consisted of enzymes, transcription factors and other intracellular signaling molecules. IL12 slightly induced preferential expression of T2BP during Th1 differentiation, whereas IL4 strongly up-regulated NDFIP2 during Th2 differentiation. These genes activate NFκB and MAPK signaling (Matsuda 2003). Moreover, IL4 regulated genes coding for GPCRs (CYSLTR1, HRH4 and GPR18) or mediators of RAS signaling (RAB27B, RAB30 and ARHQ). Numerous novel transcriptional regulators, such as RNF19, ZNF443, EPAS1, SNFT and HOP became differentially regulated during the early Th1 and Th2 cells differentiation. Also a few cell adhesion molecules (i.e. CD47), receptors and transporters (i.e. IL7R and SCN3A) were among the genes involved in the early Th1 and Th2 cell polarization. The function of the majority of the genes involved in the early Th1 and Th2 cell differentiation is unknown. Among these were, such as ESTs AI969697, AI610684, R98767 and AW629527 that were rapidly up-regulated by IL4 in the cells induced to polarize to Th2 direction. Further studies elucidating the role of these unknown factors in Th1 and Th2 cell differentiation will be highly interesting.

Genes Regulated by TGFβ During the Early Th1 or Th2 Differentiation.

To study the effects of TGFβ on the early polarization of Th cells, the cells cultured in Th1 or Th2 conditions were compared to those cultured similarly, but in the presence of TGFβ. As a result, altogether 110 genes were observed to be regulated by TGFβ. data not shown. These included 72 genes that were regulated by TGFβ and polarizing cytokines IL12 or IL4. Altogether 25 genes were co-regulated by TGFβ and IL12 (Table V). Expression of 5 genes induced by IL12 after 48 hours was enhanced in the presence of TGFβ, at least in some of the time points studied. Importantly, TGFβ antagonized the effects of IL12 on 19 genes, which were regulated in an opposite manner by IL12 and TGFβ. Similarly, effects of IL4 on the expression of altogether 20 genes were enhanced in the presence of TGFβ. whereas expression of altogether 25 genes was antagonized by TGFβ (Table VI)

A subset of genes (ZBED2, LMNA, NDFIP2, AI042152, SYTL3, SLC2A3 and C20orf97) co-regulated by TGFβ and polarizing cytokines were up-regulated by both IL12 and IL4. Of these expression of ZBED2, LMNA and NDFIP2 was further increased in the presence of TGFβ in both Th1 and Th2 conditions. Genes AI042152, SYTL3, SLC2A3 and C20orf97 up-regulated by IL12 and IL4 were repressed by TGFβ in both Th1 and Th2 conditions.

Validation of the Oligonucleotide Array Results with Real-Time RT-PCR.

Transcription factor ZNF443 and unknown DACT1, AW629527 and AA237039 were among the genes that were observed to be rapidly induced by IL4 during early Th2 polarization. To confirm the oligonucleotide array results, expression kinetics of these genes was studied during one week of Th1 and Th2 polarization with Real-Time RT-PCR. Induction by IL4 that was detected by oligonucleotide arrays was confirmed for all of these genes (FIG. 2). For the EST AW629527 the IL4-mediated up-regulation was seen also after 7 days of polarization. For the other genes the regulation by IL4 was limited within the first 2 days of Th2 differentiation.

Discussion

As a result of genome wide screening of the genes involved in the early Th1 and Th2 differentiation, numerous novel genes with known or unknown function were identified to be implicated in the process. Moreover, activation of the genes belonging to specific intracellular signaling cascades was demonstrated. This provides an overview of the intracellular signaling events in the cells at the initiation of Th1 and Th2 cell differentiation. Thp cells are not responsive to IL12, which can be seen in slow changes in gene expression profiles in response to IL12 during early Th1 cell differentiation. Activation of interferon signaling seems to be the first event during Th1 differentiation, demonstrated by the early upregulation of key regulators of Th1 differentiation IFNG, TBX21 and interferon-regulated genes GBP1 and GBP5 (unpublished data), (3, 4, 23, 24). TBX21 is known to be induced by T cell activation and enhanced IFNγ production during the early Th1 polarization (25-28). Thus, the effects of IL12 on its expression are likely to be indirect. The role of GBP1 and GBP5 in Th1 polarization is not known. As these genes are known to be induced by interferons, it is likely that similarly to TBX21, they are induced as a secondary effect due enhanced IFNγ signaling. Activation of IFNγ signaling and TBX21 expression during the early differentiation is known to be essential for the Th1 differentiation, probably because it enables IL12 signaling (4, 25, 29, 30).

The genes coding for receptor components for IL12 and IL18 (IL12RB2 and IL18RAP) are up-regulated within 48 h enhancing the responsiveness of the developing Th1 cells to Th1 polarizing cytokines (10). Concordantly, after 48 h of Th1 polarization the effects of IL12 became clear and it regulated expression of numerous genes either alone or by enhancing the effects of activation. Role of the most of these genes regulated by IL12 after 48 h of Th1 differentiation is poorly known.

Thp cells are responsive to IL4, which can be seen in rapid regulation of numerous known and unknown genes. Most of the IL4-regulated genes displayed only temporary changes at some of the time points studied. However, for a subset of the genes (AW629527, AI969697, AI610684, AW152437, AW139719, R14890, AA489100, MGC16044, CGI-72, ZNF443, RAB30, NDFIP2, CD47, AMICA, CISH, SOCS3, ELL2, FOSL2, RNF19, RNF125, ZBED2, SYTL3, SLC37A3, AA002140, AA237039, LOC285628, PALM2, DACT1, VMP1, ATP6V0A2) constant regulation by IL4 was maintained throughout the first two days. Previously, we observed similar expression pattern for the key mediators of Th2 differentiation GATA3 and MAF. Moreover, similar regulation for numerous other genes, such as BCL6, NFIL3, SATB1, SOCS1, DUSP6, IL10RA and CXCR4 with unknown or less clear function in Th1 and Th2 cell differentiation was observed (10), (unpublished data). Maintenance of the IL4-mediated regulation for these genes throughout the early Th2 cell differentiation suggests these genes to be important for the process.

The function of the most of the genes involved in early Th2 differentiation is unknown. However, some of them code for components of well-known intracellular signaling cascades. Components of RAS signaling are preferentially induced during early Th2 polarization. Genes RAB27, RAB30, ARHQ and previously identified genes RASGRP1, RASA3 and SOS1 are induced by IL4 within 2 or 6 h (unpublished data). This is concordant with previous studies that have shown RAS pathway to promote IL4R signaling and to be essential for Th2 responses in vivo (31-33). Activators of NFκB signaling NDFIP2 and MAP2K14 are also up-regulated by IL4 within 2 or 6 h, respectively (unpublished data) (34). This probably leads to activation of NFκB, which then promotes Th2 differentiation by inducing optimal expression of GATA3 and co-operates with STAT6 to regulate expression of IL4 responsive genes (35, 36). Based on current and previous studies, numerous components of GPCR signaling are rapidly regulated in response to Th2 polarizing stimuli. Genes, including GNAI1, CXCR4, PTGER2, CYSLTR1, EDG1, EBI2, FLJ11856 and HRH4 become up-regulated within 2 or 6 h and GPRK6 within 48 h. In contrast, genes CD97, PTGER4, ADORA2A, CCR7, GPR18, GPRK5 and P2Y5 are rapidly repressed by IL4 (10), (unpublished data). GPCR signaling is implicated in regulation of Th1 and Th2 responses and is known to have an important role in Th2-mediated diseases, such as asthma (37). Induction of GPCR signaling through GNAI1 can also lead to activation of RAS pathway, thus promoting IL4 signaling. Also members of SOCS family seem to be preferentially induced during early Th2 cell differentiation, as CISH (SOCS) and SOCS3 were both rapidly induced by IL4. Previously, similar induction in the expression of SOCS1 was seen (10), (unpublished data). CISH represses STAT5 signaling in response to erythropoietin, IL2 and IL3 (Yoshimura 1995). However, its role in regulation of Th1 and Th2 cell differentiation has not been directly demonstrated. In contrast, SOCS3 has been shown to enhance Th2 responses and increase airway hypersensitivity in mouse (18). Similarly to CISH, SOCS3 inhibits activation of STAT5 in response to IL2 and importantly, represses Th1 differentiation by inhibiting STAT4 phosphorylation by IL12. SOCS3 has also reported to promote activation of RAS pathway by blocking activity of inhibitor p120 RasGAP (38).

TGFβ is an immunosuppressive factor able to inhibit Th1 and Th2 cell differentiation. Concordant with our previous studies, a subset of genes was identified that were regulated in an opposite manner by TGFβ and IL12 or IL4 (10). TGFβ antagonized the effects of IL12 on genes, such as SOCS3, HOP, HIMAP4, CRACC, T2BP, CRIP1 and effects of IL4 on genes, such as SYLT3, PPAP2A and A U134997. The functional role of most of these genes in the Th cell differentiation is unknown and requires further characterization. Previously identified genes that behave in a similar manner include GZMB, NFIL3, TNFRSF9, VIM, SATB1, BCL2A1, ID2, PTGS2, PLA2G4A, GNAI1, ID3, LAMA3, CCL20, RTP801 and R32184_3 (C19orf6) (10), (unpublished data). The genes regulated by IL12 or IL4 and antagonized by TGFβ are likely to be part of the mechanism how TGFβ inhibits Th1 and Th2 differentiation. Thus, these factors may also be critical for the progression of Th1 and Th2 differentiation.

In conclusion, based on our current and previous studies altogether 297 genes or approximately 1% of the genes in whole human genome are involved in the early Th1 and Th2 polarization during the first two days. Although all of these genes are may not be important for the differentiation process, these findings imply that the regulation of the Th1 and Th2 differentiation process must be much more complex than current models have suggested. Among these novel genes are likely to be factors that are critical regulators of Th1 and Th2 differentiation process together with the previously identified factors, such as STAT4, TBX21, STAT6 and GATA3. As Th1 and Th2 cells are implicated in many immune-mediated diseases, components of these signaling pathways, such as GPCRs and cytokine signaling are attractive therapeutic targets. Applications for many candidate genes for such purposes are already under development. This study provides a detailed overview of the gene regulation during the early Th1 and Th2 cell differentiation and numerous new candidates for therapeutic target molecules.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes to the same extent as if each individual publication, patent or patent application were specifically and individually indicated to be so incorporated by reference.

TABLE I

Primers and probes used in the Real-Time RT-PCR.

| Public ID | Gene symbol | 1) 5'-6(FAM)-PROBE-(TAMRA)-3'<br>2) 5'-PRIMER 1-3'<br>3) 5'-PRIMER 2-3' |
|---|---|---|
| AA237039 | — | 1) 5'-TTTATGCAGCGCACTGTCAGACTTCCAA-3'<br>2) 5'-GATGCATCTGCTTTTAACCCTTTT-3'<br>3) 5'-TTACGGAATGCTGTGGTACTCAA-3' |
| AW629527 | — | 1) 5'-ACCCATTTTGATTGAGACCTACACAGGGC-3'<br>2) 5'-TGGAAGAGGAAAGAAACTGATGGT-3'<br>3) 5'-GCGGTTTCCAATGAATGACA-3' |
| J04617 | EF1α | 1) 5'-AGCGCCGGCTATGCCCCTG-3'<br>2) 5'-CTGAACCATCCAGGCCAAAT-3'<br>3) 5'-GCCGTGTGGCAATCCAAT-3' |
| NM_016651 | DACT1 | 1) 5'-CACGAACTCGCCCTCGCTCACACT-3'<br>2) 5'AGCAGAGCAATTACACCACCAA-3'<br>3) 5'-AGTCTGGACAAACTGGGACCAA-3' |
| NM_005815 | ZNF443 | 1) 5'-TCTCTTGGCTCACTTGCTTTCTACGACATG-3'<br>2) 5'-GAATGTAAGGAATGTGGGAAAGC-3'<br>3) 5'-CATAGGATTTCTCTCTCATGTGAATTCT-3' |

TABLE II

Genes regulated by IL12 during the early Th1 polarization.

| Public ID | Gene Symbol | Known or putative function | Fold change Th1 vs Act | | | Fold change Th1 vs Th2 | | |
|---|---|---|---|---|---|---|---|---|
| | | | 2 h | 6 h | 48 h | 2 h | 6 h | 48 h |
| NM_013351 | TBX21 | Transcriptional regulator | — | 1.6 | — | — | — | 3.2 |
| BG545653 | GBP5 | Enzyme | — | 1.4 | — | — | 2.5 | — |
| NM_016081 | KIAA0992[a] | Unknown | — | — | 8.0 | — | — | — |
| AF176013 | JDP[a,b] | Miscellaneous | — | — | 4.3 | — | — | 16.6 |
| NM_024508 | ZBED2 | Transcriptional regulator | — | — | 3.7 | — | -2.9 | — |
| BG035761 | SOCS3 | Intracellular signaling | — | — | 2.5 | — | — | — |
| AF142573 | LOC83690[a] | Unknown | — | — | 2.9 | — | — | — |
| AB059408 | HOP /// HOP | Transcriptional regulator | — | — | 2.9 | — | — | — |
| Y13786 | ADAM19 | Enzyme | — | — | 2.7 | — | — | — |
| BG110811 | LOC340061[a] | Unknown | — | — | 2.6 | — | — | — |
| NM_005572 | LMNA | Unknown | — | — | 2.5 | 1.8 | — | — |
| AV713773 | MCOLN2 | Transporter | — | — | 2.3 | — | — | — |
| BE217880 | IL7R[a] | Receptor | — | — | 2.3 | — | — | — |
| AL354872 | CTH | Enzyme | — | — | 2.2 | — | — | — |
| AI042152 | — | Unknown | — | — | 2.2 | — | — | — |
| NM_006137 | CD7 | Receptor | — | — | 2.1 | — | — | — |
| NM_018326 | HIMAP4[a] | Unknown | — | — | 2.1 | 1.9 | 2.7 | 2.5 |
| AK021850 | PBF[a] | Unknown | — | — | 2.0 | — | — | — |
| AI674404 | SYTL3 | Unknown | — | — | 1.8 | — | -5.1 | -1.9 |
| AL121985 | CRACC[a] | Unknown | — | — | 1.8 | — | — | 12.1 |
| AA831661 | MGC29814 | Unknown | — | — | 1.7 | — | — | — |
| AI631159 | SLC2A3 | Transporter | — | — | 1.7 | — | — | — |
| AW574798 | KLHL6 | Miscellaneous | — | — | 1.6 | — | — | — |
| AI214996 | LOC284018 | Unknown | — | — | 1.6 | — | -5.1 | — |
| AK026646 | SURF4 | Unknown | — | — | 1.6 | — | — | — |
| AA195074 | T2BP | Unknown | — | — | 1.6 | — | 1.7 | 2.2 |
| NM_030938 | VMP1 /// VMP1 | Unknown | — | — | 1.5 | -2.5 | — | -1.6 |
| AW150720 | RDH10 | Enzyme | — | — | 1.5 | — | — | — |
| NM_021158 | C20orf97 | Enzyme | — | — | 1.4 | — | — | — |
| AL564683 | CEBPB | Transcriptional regulator | — | — | 1.4 | — | — | — |
| AW290956 | NDFIP2 | Unknown | — | — | 1.3 | -2.2 | -1.5 | -2.3 |
| NM_001629 | ALOX5AP | Enzyme | — | — | -1.2 | — | — | — |
| AB000888 | PPAP2A[a] | Enzyme | — | — | -1.5 | — | -2.0 | -2.1 |
| AI005043 | WASPIP | Cytoskeletal | — | — | -1.7 | — | — | — |
| BF209337 | MGC4677[a] | Unknown | — | — | -1.7 | — | -1.9 | -1.6 |
| AI524095 | LY9 | Cell adhesion | — | — | -1.7 | — | 1.9 | — |

TABLE II-continued

Genes regulated by IL12 during the early Th1 polarization.

| Public ID | Gene Symbol | Known or putative function | Fold change Th1 vs Act 2 h | 6 h | 48 h | Fold change Th1 vs Th2 2 h | 6 h | 48 h |
|---|---|---|---|---|---|---|---|---|
| J03223 | PRG1[a] | Unknown | — | — | −1.9 | — | — | −2.4 |
| NM_002961 | S100A4 | Miscellaneous | — | — | −2.1 | — | — | −2.4 |
| NM_001311 | CRIP1[a] | Miscellaneous | — | — | −2.1 | — | — | −2.8 |
| BE222344 | —[a] | Unknown | — | — | −2.5 | 1.9 | — | — |
| BF968270 | FLJ37712 | Unknown | — | — | −2.8 | — | −1.6 | — |
| H99792 | —[a] | Unknown | — | — | −4.6 | — | — | — |

[a] No similar regulation by activation alone or in combination with IL4 was observed.
[b] Representative result from several different probe sets.

TABLE III

Genes regulated by IL4 at more than one time point during the early Th2 polarization (see supplement for the all of the IL4-regulated genes).

| Public ID | Gene Symbol | Known or putative function | Fold change Th2 vs Act 2 h | 6 h | 48 h | Fold change Th1 vs Th2 2 h | 6 h | 48 h |
|---|---|---|---|---|---|---|---|---|
| NM_013324 | CISH[a] | Intracellular signaling | 14.4 | 4 | 1.4 | −13 | −2.8 | — |
| AI969697 | —[b] | Unknown | 3.2 | 17.8 | 7.5 | −2.5 | −5.9 | −10.9 |
| NM_016651 | DACT1[b] | Miscellaneous | 2.9 | 2.5 | 1.9 | −2.5 | −1.9 | — |
| BF674052 | VMP1[a] | Miscellaneous | 2.9 | 1.7 | 3.2 | −3.9 | −1.8 | — |
| AL118798 | CD47[a,b] | Cell adhesion | 2.7 | 1.6 | 1.8 | −2.6 | −1.7 | −1.9 |
| BG540494 | PALM2[a,b] | Miscellaneous | 2.5 | 3.1 | 2.4 | −2.3 | −2.9 | — |
| AW290956 | NDFIP2 | Miscellaneous | 1.9 | 1.5 | 3 | −2.2 | −1.5 | −2.3 |
| AI924426 | ELL2 | Transcriptional regulator | 1.9 | 1.8 | 2.5 | −1.8 | −1.7 | — |
| AA489100 | —[b] | Unknown | 5.3 | 2.1 | — | — | −2 | — |
| AI610684 | —[b] | Unknown | 4.1 | 1.9 | — | −4.3 | −2 | — |
| NM_005815 | ZNF443[b] | Transcriptional regulator | 4 | 2.5 | — | −3.2 | −2.5 | — |
| AF225986 | SCN3A[b] | Transporter | 3.9 | 3 | — | −6.7 | −3.4 | — |
| AW152437 | — | Unknown | 3.7 | 1.6 | — | −4 | −1.7 | — |
| BF056901 | MGC16044[b] | Unknown | 3.6 | 2.3 | — | −3 | −2.6 | — |
| AW139719 | — | Unknown | 3.4 | 1.6 | — | −3.2 | −1.9 | — |
| R14890 | — | Unknown | 3.2 | 2.7 | — | −3.1 | −2.8 | — |
| AC004010 | AMIGO2 | Miscellaneous | 3.2 | 1.9 | — | −3.7 | −1.9 | — |
| R98767 | —[b] | Unknown | 3 | 1.7 | — | −4.4 | −2.1 | — |
| AL109935 | KIAA1434[b] | Enzyme | 2.9 | 2.5 | — | −2.6 | −2.5 | — |
| NM_025151 | RCP[a] | Miscellaneous | 2.8 | 2.1 | — | −3.6 | −1.8 | — |
| AK022280 | CGI-72[a,b] | Miscellaneous | 2.5 | 2.3 | — | −2.5 | −2.1 | — |
| AI797353 | FLJ31340[b] | Unknown | 2.3 | 2.5 | — | — | −2.6 | — |
| AI768674 | Na[b] | Unknown | 2.3 | 2.2 | — | — | — | — |
| AV725328 | PRNP | Miscellaneous | 2.1 | 1.7 | — | −2.1 | −1.5 | — |
| BE748563 | LOC93081[b] | Enzyme | 2.1 | 2.5 | — | −2.4 | −2.2 | — |
| AL138717 | RRAGD[b] | Enzyme | 1.9 | 2.2 | — | — | −1.7 | — |
| AA088177 | KIAA1913[b] | Unknown | 1.7 | 1.9 | — | — | −1.9 | — |
| AB033106 | KIAA1280[a,b] | Unknown | 1.7 | 3.4 | — | −1.6 | −2.8 | — |
| NM_016837 | RBMS1[b] | Nucleic acid binding | 1.4 | 2 | — | — | −1.7 | — |
| NM_017831 | RNF125[b] | Miscellaneous | 2.4 | — | 4.1 | −2.4 | — | −4.4 |
| AL048542 | AMICA | Miscellaneous | 2 | — | 3.6 | −1.8 | −1.9 | −3.9 |
| NM_012463 | ATP6V0A2 | Transporter | 1.6 | — | 3 | — | — | −4 |
| AA237039 | — | Unknown | 2.9 | — | 2.7 | −4.4 | — | −2.9 |
| AI244908 | SOCS3 | Intracellular signaling | 2.4 | — | 2.6 | −2 | — | — |
| AA002140 | —[b] | Unknown | 2.8 | — | 2.1 | −3.4 | — | — |
| AU150319 | VAMP1 | Miscellaneous | −1.5 | −2.5 | — | — | 2.4 | — |
| NM_018326 | HIMAP4[b] | Miscellaneous | −1.7 | −2.4 | — | 1.9 | 2.7 | 2.5 |
| AI654547 | — | Unknown | −1.9 | 1.6 | — | — | −1.6 | — |
| AI870617 | KAI1[b] | Miscellaneous | −2.4 | −1.9 | — | 2 | 1.4 | — |
| NM_002668 | PLP2 | Transporter | −1.4 | — | 1.5 | 1.7 | — | −1.5 |
| NM_003807 | TNFSF14 | Intracellular signaling | −1.5 | — | 2.5 | — | — | −6.1 |
| AW629527 | — | Unknown | — | 8.3 | 10.9 | — | −7.0 | −10.6 |
| AI674404 | SYTL3 | Miscellaneous | — | 3.2 | 2.8 | — | −5.1 | −1.9 |
| NM_024508 | ZBED2 | DNA binding | — | 2.9 | 3.7 | — | −2.9 | — |
| AL136583 | SLC37A3[b] | Miscellaneous | — | 2.5 | 6.3 | — | −2.5 | −4.3 |
| AI670862 | FOSL2[b] | Transcriptional regulator | — | 2.2 | 2.9 | — | −1.9 | — |
| AB029316 | RNF19 | Intracellular signaling | — | 1.4 | 3.1 | — | −1.6 | −2.1 |
| AL389942 | LOC285628[b] | Unknown | — | −3.4 | −1.7 | — | 2.5 | — |

[a] Representative result from several different probe sets.
[b] No similar regulation by activation alone or in combination with IL12 was observed.

TABLE IV

Distribution of the IL12- or IL4-regulated genes in to the different functional groups.

| | IL12-regulated genes | | | | | | IL4-regulated genes | | | | | |
|---|---|---|---|---|---|---|---|---|---|---|---|---|
| | 2 h | | 6 h | | 48 h | | 2 h | | 6 h | | 48 h | |
| Functional group | up | down | up | down | up | down | up | down | up | down | up | down |
| Receptors | — | — | — | — | 2 | — | — | — | 2 | 2 | 1 | — |
| Cell adhesion | — | — | — | — | — | 1 | 1 | — | 1 | 1 | 2 | — |
| Enzyme and enzyme inhibitors | — | — | 1 | — | 4 | 2 | 6 | — | 8 | 4 | 7 | — |
| GPCR signaling | — | — | — | — | — | — | 2 | — | 1 | 2 | — | — |
| RAS signaling | — | — | — | — | — | — | 2 | — | 1 | 0 | — | — |
| Other intracellular signaling | — | — | — | — | 1 | — | 4 | 2 | 3 | 1 | 3 | 1 |
| Transcriptional regulation | — | — | 1 | — | 3 | — | 2 | — | 6 | 1 | 9 | 1 |
| Transporters | — | — | — | — | 1 | — | 3 | 1 | 4 | 1 | 4 | — |
| Cytoskeletal | — | — | — | — | — | 1 | 1 | — | — | 1 | 2 | — |
| Unknown | — | — | — | — | 15 | 5 | 30 | 2 | 30 | 7 | 9 | 1 |
| Miscellaneous | — | — | — | — | 2 | 2 | 10 | 4 | 14 | 5 | 14 | 4 |
| All | — | — | 2 | — | 28 | 11 | 61 | 9 | 80 | 25 | 51 | 7 |

TABLE V

Genes co-regulated by IL12 and TGFβ.

| | | | Fold change Th1 + TGFβ vs Th1 | | | Fold change Th1 vs Act | | |
|---|---|---|---|---|---|---|---|---|
| Public ID | Gene Symbol | Known or putative function | 2 h | 6 h | 48 h | 2 h | 6 h | 48 h |
| NM_006137 | CD7 | Receptor | 2.1 | — | −1.6 | — | — | 2.1 |
| *TGFβ enhances the effects of IL12* | | | | | | | | |
| NM_024508 | ZBED2[a] | Miscellaneous | — | 1.7 | — | — | — | 3.7 |
| Y13786 | ADAM19 | Enzyme | — | 3.4 | — | — | — | 2.7 |
| NM_005572 | LMNA[a] | Miscellaneous | — | — | 2.1 | — | — | 2.5 |
| AW574798 | KLHL6 | Miscellaneous | 1.4 | — | — | — | — | 1.6 |
| AW290956 | NDFIP2[a] | Miscellaneous | 1.7 | — | — | — | — | 1.3 |
| *TGFβ antagonizes the effects of IL12* | | | | | | | | |
| AI244908 | SOCS3[a] | Intracellular signaling | — | — | −2.0 | — | — | 3.1 |
| AB059408 | HOP /// HOP | Transcriptional regulator | — | — | −7.0 | — | — | 2.9 |
| BG110811 | LOC340061 | Unknown | — | — | −1.5 | — | — | 2.6 |
| AV713773 | MCOLN2 | Transporter | — | — | −4.0 | — | — | 2.3 |
| AI042152 | — | Unknown | — | — | −2.5 | — | — | 2.2 |
| NM_018326 | HIMAP4[a] | Miscellaneous | — | — | −1.9 | — | — | 2.1 |
| AK021850 | PBF | Miscellaneous | — | — | −2.1 | — | — | 2.0 |
| AI674404 | SYTL3[a] | Miscellaneous | — | — | −3.2 | — | — | 1.8 |
| AL121985 | CRACC[a] | Miscellaneous | — | — | −2.5 | — | — | 1.8 |
| AA831661 | MGC29814 | Unknown | — | — | −2.1 | — | — | 1.7 |
| AI631159 | SLC2A3 | Transporter | — | — | −2.5 | — | — | 1.7 |
| AI214996 | LOC2840181[a] | Unknown | — | — | −1.6 | — | — | 1.6 |
| AA195074 | T2BP[a] | Miscellaneous | — | — | −1.6 | — | — | 1.6 |
| AW150720 | RDH10 | Enzyme | — | — | −2.3 | — | — | 1.5 |
| NM_021158 | C20orf97 | Enzyme | — | — | −2.5 | — | — | 1.4 |
| NM_001629 | ALOX5AP | Enzyme | — | — | 2.2 | — | — | −1.2 |
| BF209337 | MGC4677[a] | Unknown | — | 1.9 | 1.7 | — | — | −1.7 |
| BE222344 | —[a] | Unknown | — | 1.7 | 5.1 | — | — | −2.5 |
| NM_001311 | CRIP1[a] | Miscellaneous | — | — | 3.0 | — | — | −2.1 |

[a]Differential expression by the cells induced to polarize to Th1 and Th2 direction.

TABLE VI

Genes co-regulated by TGFβ and IL4.

| | | | Fold change Th2 + TGFβ vs Th2 | | | Fold change Th2 vs Act | | |
|---|---|---|---|---|---|---|---|---|
| Public ID | Gene Symbol | Known or putative function | 2 h | 6 h | 48 h | 2 h | 6 h | 48 h |
| AF053712 | TNFSF11[a] | Intracellular signaling | — | 1.7 | — | — | 1.7 | — |
| AF261135 | GPR18[a] | GPCR signaling | — | 1.5 | −1.9 | — | −1.6 | — |
| *TGFβ enhances the effects of IL4* | | | | | | | | |

TABLE VI-continued

Genes co-regulated by TGFβ and IL4.

| Public ID | Gene Symbol | Known or putative function | Fold change Th2 + TGFβ vs Th2 | | | Fold change Th2 vs Act | | |
|---|---|---|---|---|---|---|---|---|
| | | | 2 h | 6 h | 48 h | 2 h | 6 h | 48 h |
| AW290956 | NDFIP2[a] | Miscellaneous | 1.3 | — | — | 1.9 | 1.5 | 3.0 |
| AI924426 | ELL2[a] | Transcriptional regulator | — | 2.3 | — | 1.9 | 1.8 | 2.5 |
| W72060 | —[a] | Unknown | — | 1.5 | — | 1.5 | — | — |
| AA088177 | KIAA1913[a] | Unknown | — | — | 2.5 | 1.7 | 1.9 | — |
| BF439618 | CD47[a] | Cell adhesion | — | — | 1.6 | 2.3 | — | — |
| AL048542 | AMICA[a] | Miscellaneous | — | — | 1.6 | 2.0 | — | 3.6 |
| AL118798 | CD471 | Cell adhesion | — | — | 1.5 | 2.7 | 1.6 | 1.8 |
| NM_001924 | GADD45A[a] | Intracellular signaling | — | — | -2.2 | -1.7 | — | — |
| BF209337 | MGC4677[a] | Unknown | 1.5 | 1.6 | — | — | 1.5 | — |
| NM_024508 | ZBED2[a] | DNA binding | — | 2.2 | — | — | 2.9 | 3.7 |
| AA149648 | FLT1[a] | Receptor, enzyme | — | 1.4 | — | — | 2.8 | — |
| AA029441 | CAMK2D[a] | Enzyme | — | — | 1.3 | — | 2.2 | — |
| AI524095 | LY9[a] | Cell adhesion | — | — | -1.9 | — | -2.5 | — |
| NM_004369 | COL6A3[a] | Enzyme inhibitor, cell adhesion | — | 3.1 | — | — | — | 13.5 |
| AL110164 | LIMS1 | Miscellaneous | — | 2.5 | — | — | — | 1.6 |
| AF101051 | CLDN1[a] | Cell adhesion | — | 1.3 | — | — | — | 2.5 |
| AW591809 | —[a] | Miscellaneous | — | — | 2.8 | — | — | 3.4 |
| AL513759 | RBPSUH[a] | Transcriptional regulator | — | — | 2.4 | — | — | 1.8 |
| NM_005572 | LMNA[a] | Miscellaneous | — | — | 3.1 | — | — | 1.5 |
| U57059 | TNFSF10 | Intracellular signaling | — | — | -2.4 | — | — | -1.9 |
| TGFβ antagonizes the effects of IL4 | | | | | | | | |
| AW135176 | —[a] | Miscellaneous | -2.2 | — | — | 4.3 | — | — |
| AW152437 | —[a] | Unknown | -1.4 | — | — | 3.7 | 1.6 | — |
| AI654547 | —[a] | Unknown | 1.3 | 1.5 | — | -1.9 | 1.6 | — |
| NM_002668 | PLP2[a] | Transporter | 1.5 | 1.8 | 1.6 | -1.4 | — | 1.5 |
| AL035541 | TMEPAI[a] | Miscellaneous | 1.8 | 2.7 | — | -1.6 | — | — |
| AA854943 | ANKH | Transporter | 1.3 | 1.6 | — | — | -1.4 | — |
| AI798823 | PSCD1[a] | Transporter | — | -3.6 | — | — | 5.9 | — |
| AI825833 | — | Unknown | — | -2.7 | — | — | 1.7 | — |
| AI674404 | SYTL3[a] | Miscellaneous | — | -2.3 | -4.1 | — | 3.2 | 2.8 |
| AB000888 | PPAP2A[a] | Enzyme | — | -1.9 | -1.9 | — | 2.4 | — |
| AW629527 | — | Unknown | — | — | -1.5 | — | 8.3 | 10.9 |
| AI823980 | RBSK | Enzyme | — | — | -2.5 | — | — | 4.0 |
| NM_021158 | C20orf97 | Enzyme | — | — | -2.5 | — | — | 1.8 |
| AU134977 | — | Unknown | — | — | -2.3 | — | — | 2.0 |
| AI042152 | — | Unknown | — | — | -2.1 | — | — | 1.9 |
| AL564683 | CEBPB | Transcriptional regulator | — | — | -2.1 | — | — | 1.7 |
| NM_018664 | SNFT[a] | Transcriptional regulator | — | — | -2.0 | — | — | 4.3 |
| AI342543 | FLJ33069[a] | Unknown | — | — | -1.9 | — | — | 2.8 |
| BG171548 | NCE2[a] | Enzyme | — | — | -1.7 | — | — | 1.9 |
| AL353944 | —[a] | Unknown | — | — | -1.6 | — | — | 2.7 |
| AL563795 | MGC23937[a] | Enzyme | — | — | -1.6 | — | — | 2.1 |
| AI631159 | SLC2A3 | Transporter | — | — | -1.6 | — | — | 1.6 |
| AA352113 | SIAT8D | Enzyme | — | — | -1.4 | — | — | 2.3 |
| BC002827 | TPM4[a] | Cytoskeletal | — | — | -1.4 | — | — | 2.1 |
| BF968270 | FLJ37712[a] | Unknown | — | — | 2.1 | — | — | -1.8 |

[a]Differential expression by the cells induced to polarize to Th1 and Th2 direction.

TABLE 7

Genes regulated by IL4 at one time point during early Th2 differentiation.

| Public ID | Gene Symbol | Known or putative function | Fold change Th2 vs Act | | | Fold change Th1 vs Th2 | | |
|---|---|---|---|---|---|---|---|---|
| | | | 2 h | 6 h | 48 h | 2 h | 6 h | 48 h |
| AA551075 | LOC115207[a] | Transporter | 1.6 | — | — | -3.2 | — | — |
| AW294640 | RAB30[a] | RAS signaling | 3.0 | — | — | -3.4 | — | — |
| BF670447 | ARHQ[a] | RAS signaling | 2.1 | — | — | -2.8 | — | — |
| AI458439 | — | Unknown | 1.8 | — | — | -2.4 | — | -2.8 |
| AA830854 | — | Unknown | 2.2 | — | — | -2.0 | — | — |
| W72060 | — | Unknown | 1.5 | — | — | -1.6 | — | — |
| AA429262 | —[a] | Unknown | 3.0 | — | — | -4.1 | — | — |
| AW135176 | — | Unknown | 4.3 | — | — | -2.8 | — | — |
| AI221707 | —[a] | Unknown | 2.6 | — | — | -2.7 | — | — |
| AK023816 | —[a] | Unknown | 1.8 | — | — | -2.1 | — | — |
| AI888503 | —[a] | Unknown | 2.4 | — | — | -2.5 | — | — |

TABLE 7-continued

Genes regulated by IL4 at one time point during early Th2 differentiation.

| Public ID | Gene Symbol | Known or putative function | Fold change Th2 vs Act | | | Fold change Th1 vs Th2 | | |
|---|---|---|---|---|---|---|---|---|
| | | | 2 h | 6 h | 48 h | 2 h | 6 h | 48 h |
| AW070573 | —[a] | Unknown | 3.9 | — | — | −2.8 | — | — |
| AW292872 | — | Unknown | 2.1 | — | — | −2.1 | — | −1.6 |
| BF968097 | —[a] | Unknown | 3.5 | — | — | −12 | — | — |
| AI494573 | —[a] | Unknown | 3.7 | — | — | −3.5 | — | — |
| NM_024048 | MGC3020[a] | Unknown | 2.7 | — | — | −3.0 | — | — |
| BG485129 | —[a] | Unknown | 2.1 | — | — | −1.5 | — | — |
| AW205964 | —[a] | Unknown | 2.9 | — | — | −2.8 | — | — |
| AA034012 | —[a] | Unknown | 2.4 | — | — | −2.8 | — | — |
| AL117381 | BCL2L1 | Intracellular signaling | 2.2 | — | — | — | — | — |
| NM_013322 | SNX10 | Intracellular signaling | 1.9 | — | — | −2.1 | — | — |
| AU159276 | CYSLTR1[a,b] | GPCR signaling | 2.7 | — | — | −3.0 | — | — |
| NM_021178 | C14orf18 | Enzyme | 2.5 | — | — | −1.9 | — | — |
| NM_017719 | SNRK[a] | Enzyme | 2.2 | — | — | — | — | — |
| BF739767 | DKFZp761P0423[a] | Enzyme | 2.5 | — | — | — | — | — |
| AK022771 | TUBD1[a] | Cytoskeletal | 1.9 | — | — | −2.1 | — | — |
| NM_002668 | PLP2 | Transporter | −1.4 | — | 1.5 | 1.7 | — | −1.5 |
| NM_003807 | TNFSF14 | Intracellular signaling | −1.5 | — | 2.5 | — | — | −6.1 |
| AL035541 | TMEPAI[a] | Miscellaneous | −1.6 | — | — | 1.4 | — | — |
| NM_001924 | GADD45A | Intracellular signaling | −1.7 | — | — | 1.3 | — | — |
| AI681671 | —[a] | Unknown | −2.1 | — | — | — | — | — |
| AI798823 | PSCD1[a] | Transporter | — | 5.9 | — | — | −4.3 | — |
| AI214996 | LOC284018 | Unknown | — | 4.8 | — | — | −5.1 | — |
| AF312230 | HRH4[a] | GPCR signaling | — | 3.9 | — | — | −3.5 | — |
| AF052094 | EPAS1[a] | Transcriptional regulator | — | 3.5 | — | — | −3.5 | — |
| AA149648 | FLT1[b] | Receptor, enzyme | — | 2.8 | — | — | −3.1 | — |
| BG170541 | MET[a] | Enzyme | — | 2.7 | — | — | −5.1 | — |
| AK025100 | SNTB1[a] | Intracellular signaling | — | 2.5 | — | — | −2.2 | — |
| BF438386 | RAB27B[a] | RAS signaling | — | 2.5 | — | — | −2.1 | — |
| NM_000572 | IL10[a] | Cytokine | — | 2.5 | — | — | — | — |
| AI742057 | LOC129607[a] | Unknown | — | 2.5 | — | — | −2.1 | — |
| AW193698 | TGFBR3[a] | Receptor, TGFβ signaling | — | 2.5 | — | — | −2.0 | — |
| AI310524 | NIPA1 | Miscellaneous | — | 2.4 | — | — | −2.6 | — |
| AB000888 | PPAP2A | Enzyme | — | 2.4 | — | — | −2.0 | −2.1 |
| AL574184 | HPGD[a] | Transporter, enzyme | — | 2.2 | — | — | — | — |
| AA029441 | CAMK2D[b] | Enzyme | — | 2.2 | — | — | −2.4 | — |
| BE670307 | —[a] | Unknown | — | 2.2 | — | — | −2.3 | — |
| BE676408 | HECA[a] | Transporter | — | 2.1 | — | — | — | — |
| AI890347 | TUWD12[a] | Miscellaneous | — | 2.0 | — | −2.8 | — | — |
| AI825833 | — | Miscellaneous | — | 1.7 | — | — | — | — |
| AF053712 | TNFSF11 | Intracellular signaling | — | 1.7 | — | −1.6 | −1.7 | — |
| AA922068 | — | Unknown | — | 1.7 | — | — | −2.0 | — |
| BF037662 | —[a] | Unknown | — | 1.5 | — | −1.7 | −2.0 | −7.7 |
| NM_006226 | PLCL1[a] | Enzyme | — | 1.5 | — | — | — | — |
| BF209337 | MGC4677 | Unknown | — | 1.5 | — | — | −1.9 | −1.6 |
| NM_000100 | CSTB | Enzyme inhibitor | — | 1.4 | — | — | — | −2.1 |
| BE675435 | COPEB[a] | Miscellaneous | — | 7.5 | — | — | −5.9 | — |
| BE217880 | IL7R | Receptor | — | −1.4 | — | — | — | — |
| AA854943 | ANKH[a] | Transporter | — | −1.4 | — | — | — | — |
| AF261135 | GPR18 | GPCR signaling | — | −1.6 | — | — | — | −2.2 |
| AK027071 | TSC22 | Transcriptional regulator | — | −1.6 | — | — | 1.6 | 2.2 |
| BG545653 | GBP5[a] | Enzyme | — | −1.8 | — | — | 2.5 | — |
| NM_001838 | CCR7 | Receptor, GPCR signaling | — | −2.0 | — | 1.5 | 2.1 | — |
| D50925 | PASK | Enzyme, intracellular signaling | — | −2.0 | — | — | 1.7 | — |
| NM_023037 | 13CDNA73[a] | Miscellaneous | — | −2.0 | — | — | 1.9 | — |
| AI005043 | WASPIP | Cytoskeletal | — | −2.1 | — | — | — | — |
| AI631833 | —[a] | Unknown | — | −2.1 | — | — | 1.9 | — |
| AL136680 | GBP3[a] | Enzyme | — | −2.1 | — | — | 2.1 | — |
| AI701905 | —[a] | Unknown | — | −2.1 | — | — | 1.6 | — |
| BF589359 | PAG | Intracellular signaling | — | −2.1 | — | — | 1.7 | — |
| AA523939 | — | Unknown | — | −2.1 | — | — | 1.5 | — |
| AW340595 | — | Unknown | — | −2.2 | — | — | 1.6 | — |
| AA736452 | FLJ32029[a] | Enzyme | — | −2.3 | — | — | 1.9 | — |
| AI380089 | —[a] | Unknown | — | −2.4 | — | — | 2.0 | — |
| AI524095 | LY9 | Cell adhesion | — | −2.5 | — | — | 1.9 | — |
| AA858297 | hIAN7 | Miscellaneous | — | −2.5 | — | — | 2.9 | — |
| AI923633 | —[a] | Unknown | — | −2.7 | — | — | 1.9 | — |
| AW273811 | LOC92906[a] | Nucleic acid binding | — | −2.9 | — | — | 2.5 | — |
| NM_024711 | hIAN2 | Miscellaneous | — | −4.0 | — | — | 4.1 | — |
| AW299558 | FRBZ1[a] | Protein binding | — | −4.1 | — | — | 4.1 | — |
| NM_004369 | COL6A3 | Enzyme inhibitor, cell adhesion | — | — | 13.5 | — | 1.9 | −6.3 |
| BF739885 | SETBP1[a] | Transcriptional regulator, transporter | — | — | 5.9 | — | — | — |
| AB003476 | AKAP12[a] | Transporter | — | — | 4.6 | — | — | −5.1 |

TABLE 7-continued

Genes regulated by IL4 at one time point during early Th2 differentiation.

| Public ID | Gene Symbol | Known or putative function | Fold change Th2 vs Act | | | Fold change Th1 vs Th2 | | |
|---|---|---|---|---|---|---|---|---|
| | | | 2 h | 6 h | 48 h | 2 h | 6 h | 48 h |
| NM_018664 | SNFT[a] | Transcriptional regulator | — | — | 4.3 | — | — | -2.3 |
| AI823980 | RBSK[a] | Enzyme | — | — | 4.0 | — | — | — |
| NM_016008 | D2LIC[a] | Miscellaneous | — | — | 3.7 | — | — | — |
| AF308301 | MRPS26[a] | Miscellaneous | — | — | 3.5 | — | — | -3.1 |
| AF101051 | CLDN1[b] | Cell adhesion | — | — | 2.5 | — | -1.5 | -1.9 |
| AW591809 | —[a] | Unknown | — | — | 3.4 | — | — | -3.6 |
| AB059408 | HOP /// HOP | Transcriptional regulator | — | — | 3.2 | — | — | — |
| BC001247 | EPLIN[a,b] | Cytoskeletal | — | — | 2.9 | — | — | -4.9 |
| AI342543 | FLJ33069 | Miscellaneous | — | — | 2.8 | — | — | -2.5 |
| AL353944 | —[a] | Unknown | — | — | 2.7 | — | — | -3.5 |
| AW204712 | LOC170371[a] | Miscellaneous | — | — | 2.5 | — | — | -2.1 |
| AW574798 | KLHL6 | Protein binding | — | — | 2.3 | — | — | — |
| AA352113 | SIAT8D | Enzyme | — | — | 2.3 | — | — | — |
| BF969397 | — | Unknown | — | — | 2.2 | — | — | -2.7 |
| AK026646 | SURF4 | Miscellaneous | — | — | 2.2 | — | — | — |
| AL563795 | MGC23937 | Enzyme | — | — | 2.1 | — | — | -2.0 |
| BC002827 | TPM4[a] | Cytoskeletal | — | — | 2.1 | — | — | -1.7 |
| AL121905 | PTPRA[a] | Enzyme | — | — | 2.1 | — | — | — |
| AU134977 | —[a] | Unknown | — | — | 2.0 | — | — | — |
| NM_006137 | CD7 | Receptor | — | — | 2.0 | — | — | — |
| AI042152 | — | Unknown | — | — | 1.9 | — | — | — |
| BG171548 | NCE2 | Enzyme | — | — | 1.9 | — | — | -3.0 |
| AL513759 | RBPSUH | Transcriptional regulator | — | — | 1.8 | — | — | -1.3 |
| NM_021158 | C20orf97 | Enzyme | — | — | 1.8 | — | — | — |
| AL564683 | CEBPB | Transcriptional regulator | — | — | 1.7 | — | — | — |
| AL110164 | LIMS1[a] | Miscellaneous | — | — | 1.6 | — | — | — |
| AI631159 | SLC2A3 | Transporter | — | — | 1.6 | — | — | — |
| NM_005572 | LMNA | Miscellaneous | — | — | 1.5 | 1.8 | — | — |
| NM_013351 | TBX21[a] | Transcriptional regulator | — | — | -1.5 | — | — | 3.2 |
| BF968270 | FLJ37712 | Miscellaneous | — | — | -1.8 | — | -1.6 | — |
| U57059 | TNFSF10 | Intracellular signaling | — | — | -1.9 | — | — | — |
| NM_014751 | MTSS1 | Miscellaneous | — | — | -2.6 | — | — | — |
| NM_022873 | G1P3[a] | Miscellaneous | — | — | -2.8 | — | — | — |
| AF000426 | LST1[a] | Miscellaneous | — | — | -4.9 | — | — | — |

[a]No similar regulation by activation alone or in combination with IL4 was observed.
[b]Representative result from several different probe sets.

REFERENCES

1. Romagnani, S. 1996. Th1 and Th2 in human diseases. *Clin Immunol Immunopathol* 80, no. 3 Pt 1:225.
2. Glimcher, L. H., and K. M. Murphy. 2000. Lineage commitment in the immune system: the T helper lymphocyte grows up. *Genes & Development* 14:1693.
3. Szabo, S. J., S. T. Kim, G. L. Costa, X. Zhang, C. G. Fathman, and L. H. Glimcher. 2000. A novel transcription factor, T-bet, directs Th1 lineage commitment. *Cell* 100, no. 6:655.
4. Szabo, S. J., B. M. Sullivan, C. Stemmann, A. R. Satoskar, B. P. Sleckman, and L. H. Glimcher. 2002. Distinct effects of T-bet in TH1 lineage commitment and IFN-gamma production in CD4 and CD8 T cells. *Science* 295, no. 5553: 338.
5. Zhang, D. H., L. Cohn, P. Ray, K. Bottomly, and A. Ray. 1997. Transcription factor GATA-3 is differentially expressed in murine Th1 and Th2 cells and controls Th2-specific expression of the interleukin-5 gene. *J Biol Chem* 272, no. 34:21597.
6. Zheng, W., and R. A. Flavell. 1997. The transcription factor GATA-3 is necessary and sufficient for Th2 cytokine gene expression in CD4 T cells. *Cell* 89, no. 4:587.
7. Hamalainen, H., H. Zhou, W. Chou, H. Hashizume, R. Heller, and R. Lahesmaa. 2001. Distinct gene expression profiles of human type 1 and type 2 T helper cells. *Genome Biol* 2, no. 7.
8. Rogge, L., E. Bianchi, M. Biffi, E. Bono, S. Y. Chang, H. Alexander, C. Santini, G. Ferrari, L. Sinigaglia, M. Seiler, M. Neeb, J. Mous, F. Sinigaglia, and U. Certa. 2000. Transcript imaging of the development of human T helper cells using oligonucleotide arrays. *Nat Genet* 25, no. 1:96.
9. Lu, B., P. Zagouras, J. E. Fischer, J. Lu, B. Li, and R. A. Flavell. 2004. Kinetic analysis of genomewide gene expression reveals molecule circuitries that control T cell activation and Th1/2 differentiation. *Proc Natl Acad Sci USA* 101, no. 9:3023.
10. Lund, R., T. Aittokallio, O. Nevalainen, and R. Lahesmaa. 2003. Identification of novel genes regulated by IL-12, IL-4, or TGF-beta during the early polarization of CD4+ lymphocytes. *J Immunol* 171, no. 10:5328.
11. Lund, R. J., E. K. Ylikoski, T. Aittokallio, O. Nevalainen, and R. Lahesmaa. 2003. Kinetics and STAT4- or STAT6-mediated regulation of genes involved in lymphocyte polarization to Th1 and Th2 cells. *Eur J Immunol* 33, no. 4:1105.
12. Chen, Z., R. Lund, T. Aittokallio, M. Kosonen, O. Nevalainen, and R. Lahesmaa. 2003. Identification of Novel IL-4/Stat6-Regulated Genes in T Lymphocytes. *J Immunol* 171, no. 7:In press.
13. Chtanova, T., R. A. Kemp, A. P. Sutherland, F. Ronchese, and C. R. Mackay. 2001. Gene microarrays reveal extensive differential gene expression in both cd4(+) and cd8(+) type 1 and type 2 t cells. *J Immunol* 167, no. 6:3057.

14. Hoey, T., S. Zhang, N. Schmidt, Q. Yu, S. Ramchandani, X. Xu, L. K. Naeger, Y. L. Sun, and M. H. Kaplan. 2003. Distinct requirements for the naturally occurring splice forms Stat4alpha and Stat4beta in IL-12 responses. *EMBO J* 22, no. 16:4237.

15. Hamalainen, H. K., J. C. Tubman, S. Vikman, T. Kyrola, E. Ylikoski, J. A. Warrington, and R. Lahesmaa. 2001. Validation of endogenous reference genes for profiling of lymphocyte differentiation by quantitative real-time RT-PCR. *Anal Biochem* 299, no. 1:63.

16. Liu, G., A. E. Loraine, R. Shigeta, M. Cline, J. Cheng, V. Valmeekam, S. Sun, D. Kulp, and M. A. Siani-Rose. 2003. NetAffx: Affymetrix probesets and annotations. *Nucleic Acids Res* 31, no. 1:82.

17. Lund, R. J., Z. Chen, J. Scheinin, and R. Lahesmaa. 2004. Early target genes of IL-12 and STAT4 signaling in th cells. *J Immunol* 172, no. 11:6775.

18. Seki, Y., H. Inoue, N. Nagata, K. Hayashi, S. Fukuyama, K. Matsumoto, O. Komine, S. Hamano, K. Himeno, K. Inagaki-Ohara, N. Cacalano, A. O'Garra, T. Oshida, H. Saito, J. A. Johnston, A. Yoshimura, and M. Kubo. 2003. SOCS-3 regulates onset and maintenance of T(H)2-mediated allergic responses. *Nat Med* 9, no. 8:1047.

19. Li-Weber, M., O. Laur, I. Davydov, C. Hu, P. Salgame, and P. H. Krammer. 1997. What controls tissue-specific expression of the IL-4 gene? *Immunobiology* 198, no. 1-3:170.

20. Avice, M. N., M. Rubio, M. Sergerie, G. Delespesse, and M. Sarfati. 2000. CD47 ligation selectively inhibits the development of human naive T cells into Th1 effectors. *J Immunol* 165, no. 8:4624.

21. Rincon, M., and R. A. Flavell. 1999. Reprogramming transcription during the differentiation of precursor CD4+ T cells into effector Th1 and Th2 cells. *Microbes Infect* 1, no. 1:43.

22. Nagai, S., S. Hashimoto, T. Yamashita, N. Toyoda, T. Satoh, T. Suzuki, and K. Matsushima. 2001. Comprehensive gene expression profile of human activated T(h)1- and T(h)2-polarized cells. *Int Immunol* 13, no. 3:367.

23. Bradley, L. M., D. K. Dalton, and M. Croft. 1996. A direct role for IFN-gamma in regulation of Th1 cell development. *J Immunol* 157, no. 4:1350.

24. Wenner, C. A., M. L. Guler, S. E. Macatonia, A. O'Garra, and K. M. Murphy. 1996. Roles of IFN-gamma and IFN-alpha in IL-12-induced T helper cell-1 development. *J Immunol* 156, no. 4:1442.

25. Afkarian, M., J. R. Sedy, J. Yang, N. G. Jacobson, N. Cereb, S. Y. Yang, T. L. Murphy, and K. M. Murphy. 2002. T-bet is a STAT1-induced regulator of IL-12R expression in naive CD4+ T cells. *Nat Immunol* 3, no. 6:549.

26. Grogan, J. L., M. Mohrs, B. Harmon, D. A. Lacy, J. W. Sedat, and R. M. Locksley. 2001. Early transcription and silencing of cytokine genes underlie polarization of T helper cell subsets. *Immunity* 14, no. 3:205.

27. Mullen, A. C., F. A. High, A. S. Hutchins, H. W. Lee, A. V. Villarino, D. M. Livingston, A. L. Kung, N. Cereb, T. P. Yao, S. Y. Yang, and S. L. Reiner. 2001. Role of T-bet in Commitment of TH1 Cells Before IL-12-Dependent Selection. *Science* 292, no. 5523:1907.

28. Lighvani, A. A., D. M. Frucht, D. Jankovic, H. Yamane, J. Aliberti, B. D. Hissong, B. V. Nguyen, M. Gadina, A. Sher, W. E. Paul, and J. J. O'Shea. 2001. T-bet is rapidly induced by interferon-gamma in lymphoid and myeloid cells. *Proc Natl Acad Sci USA* 98, no. 26:15137.

29. Tau, G. Z., T. von der Weid, B. Lu, S. Cowan, M. Kvatyuk, A. Pernis, G. Cattoretti, N. S. Braunstein, R. L. Coffman, and P. B. Rothman. 2000. Interferon gamma signaling alters the function of T helper type 1 cells. *J Exp Med* 192, no. 7:977.

30. Gollob, J. A., H. Kawasaki, and J. Ritz. 1997. Interferon-gamma and interleukin-4 regulate T cell interleukin-12 responsiveness through the differential modulation of high-affinity interleukin-12 receptor expression. *Eur J Immunol* 27, no. 3:647.

31. Yamashita, M., M. Kimura, M. Kubo, C. Shimizu, T. Tada, R. M. Perlmutter, and T. Nakayama. 1999. T cell antigen receptor-mediated activation of the Ras/mitogen-activated protein kinase pathway controls interleukin 4 receptor function and type-2 helper T cell differentiation. *Proc Natl Acad Sci USA* 96, no. 3:1024.

32. Yamashita, M., M. Katsumata, M. Iwashima, M. Kimura, C. Shimizu, T. Kamata, T. Shin, N. Seki, S. Suzuki, M. Taniguchi, and T. Nakayama. 2000. T cell receptor-induced calcineurin activation regulates T helper type 2 cell development by modifying the interleukin 4 receptor signaling complex. *J Exp Med* 191, no. 11:1869.

33. Shibata, Y., T. Kamata, M. Kimura, M. Yamashita, C. R. Wang, K. Murata, M. Miyazaki, M. Taniguchi, N. Watanabe, and T. Nakayama. 2002. Ras activation in T cells determines the development of antigen-induced airway hyperresponsiveness and eosinophilic inflammation. *J Immunol* 169, no. 4:2134.

34. Matsuda, A., Y. Suzuki, G. Honda, S. Muramatsu, O. Matsuzaki, Y. Nagano, T. Doi, K. Shimotohno, T. Harada, E. Nishida, H. Hayashi, and S. Sugano. 2003. Large-scale identification and characterization of human genes that activate NF-kappaB and MAPK signaling pathways. *Oncogene* 22, no. 21:3307.

35. Das, J., C. H. Chen, L. Yang, L. Cohn, P. Ray, and A. Ray. 2001. A critical role for NF-kappa B in GATA3 expression and TH2 differentiation in allergic airway inflammation. *Nat Immunol* 2, no. 1:45.

36. Shen, C. H., and J. Stavnezer. 1998. Interaction of stat6 and NF-kappaB: direct association and synergistic activation of interleukin-4-induced transcription. *Mol Cell Biol* 18, no. 6:3395.

37. Johnson, E. N., and K. M. Druey. 2002. Heterotrimeric G protein signaling: role in asthma and allergic inflammation. *J Allergy Clin Immunol* 109, no. 4:592.

38. Cacalano, N. A., D. Sanden, and J. A. Johnston. 2001. Tyrosine-phosphorylated SOCS-3 inhibits STAT activation but binds to p120 RasGAP and activates Ras. *Nat Cell Biol* 3, no. 5:460.

The invention claimed is:

1. A method of identifying a compound capable of modulating the Th2 polarization of CD4+ lymphocytes, the method comprising:
   (a) contacting said compound with naïve CD4+ lymphocytes;
   (b) inducing the Th2 polarization of the lymphocytes by contacting said lymphocytes with IL-4;
   (c) preparing a gene expression profile comprising one or more genes selected from the group consisting of: AW629527, AI969697, AI610684, AW152437, AW139719, R14890, AA489100, MGC16044, CGI-72, and ZNF443, from the lymphocytes;
   (d) comparing the lymphocyte gene expression profile obtained from step (c) to a gene expression profile obtained from lymphocytes contacted with IL-4 but not contacted with the compound, wherein said gene expression profiles of steps (c) and (d) comprise the expression of the selected gene(s);

(e) wherein a difference in the level of expression of the selected gene(s) in the expression profile of step (c) compared to the expression profile of step (d) indicates that the compound modulates the Th2 polarization of CD4+ lymphocytes.

2. The method according to claim 1, wherein a difference in the expression profiles identifies a potential drug compound for the treatment of asthma, and/or allergic response.

3. A method according to claim 1, wherein said gene expression profile further comprises one or more genes selected from the group consisting of: RAB30, NDFIP2, CD47, AMICA, CISH, SOCS3, ELL2, FOSL2, RNF19, RNF125, ZBED2, SYTL3, SLC37A3, AA002140, AA237039, LOC285628, PALM2, DACT1, VMP1, and ATP6V0A2.

4. The method according to claim 1, wherein said gene expression profile further comprises one or more genes selected from the group consisting of: BCL2L11, TNFSF14, and R98767.

5. The method according to claim 1, wherein a difference in the expression profiles identifies a potential drug compound for the treatment of asthma.

* * * * *